(12) United States Patent
Gupta-Bansal et al.

(10) Patent No.: US 6,333,034 B1
(45) Date of Patent: Dec. 25, 2001

(54) PROCESS FOR INHIBITING COMPLEMENT ACTIVATION VIA THE ALTERNATIVE PATHWAY

(75) Inventors: Rekha Gupta-Bansal, Twinsburg; Kurt R. Brunden, Aurora; James B. Parent, Cleveland, all of OH (US)

(73) Assignee: Gliatech, Inc., Cleveland, OH (US)

( * ) Notice: Subject to any disclaimer, the term of this patent is extended or adjusted under 35 U.S.C. 154(b) by 0 days.

(21) Appl. No.: 09/138,723

(22) Filed: Aug. 24, 1998

Related U.S. Application Data

(63) Continuation-in-part of application No. 08/918,349, filed on Aug. 26, 1997, now abandoned.

(51) Int. Cl.$^7$ .......................... A61K 39/395; A61K 38/17
(52) U.S. Cl. ...................................... 424/139.1; 424/130.1; 514/8
(58) Field of Search .............................. 424/130.1, 145.1, 424/139.1; 514/8

(56) References Cited

FOREIGN PATENT DOCUMENTS

WO 95/25540    9/1995  (WO).

OTHER PUBLICATIONS

Sahu et al. J. Immunol 157:884–891, 1996.*
Janway and Travers Immunobiology Third Edition, Current Biology Ltd, Middlsex House, London, 1996.*
Gonzalez–Rubio, "The Inhibitory Effect of Factor J on the Alternative Complement Pathway," *The Journal of Biological Chemistry*, 269(42):26017–26024 (1994).
Huemer, et al., "Herpes simplex virus glycoprotein C molecular mimicry of complement regulatory proteins by a viral protein," *Immunology* 79(4):639–647 (1993).
Fearon, "Identification of the Membrane Glycoprotein that is the C3b Receptor of the Human Erythrocyte Polymorphonuclear Leukocyte, B Lymphocyte, and Monocyte," *J. Exp. Med.*, 152(1);20–30 (1980).
Whiteman, et al., "Association of Activated Properdin with Complexes of Properdin with C3," *The Journal of Immunology*, 147(4):1344–1351 (1991).
Alzenz, et al., "Structure and Function Analysis of C3 from Different Species," *Complement Inflamm.*, 6:307–308 (1989).
Amsterdam, et al., "Limitation of reperfusion injury by a monoclonal antibody to C5a during myocardial infarction in pigs," *Amer. J. Physiol.*, 268:H448–H457 (1995).
Anner, et al., "Pulmonary Hypertension and Leukosequestration after Lower Torsoe Ischemia," *Ann. Surgery*, 206:642–648 (1987).
Arroyaue, et al., "Mechanism of complement activation by radiographic contrast media," *Clin. Exp. Immunol.*, 29:89–94 (1977).

Bengston, et al., "Anaphylatoxin Formation in Sepsis," *Arch. Surg.*, 123:645–649 (May, 1988).
Biesecker, et al., "Inhibition of Acute Passive Transfer Experimental Autoimmune Myasthenia Gravis with Fab Antibody to Complement C6$^1$," *J. Immunol.*, 142;2654–2659 (1989).
Bjornson, et al., "Reduction in Alternative Complement Pathway Mediated C3 Conversion following Burn Injury," *Ann. Surg.*, 194:224–231 (1981).
Blondin, et al., "Inhibition of Complement Activation by Natural Sulfated Polysaccharides (Fucans) from Brown Seaweed," *Molecular Immunology*, 31(4):247–253 (1994).
Brandtzaeg, et al., "The Excessive Complement Activation in Fulminant Meningococcal Septicemia Is Predominantly Caused by Alternative Pathway Activation," *J. Infect. Dis.*, 173:647–655 (1996).
Brower, et al., "Alpha–1–Antitrypsin–Human Leukocyte Elastase Complexes in Blood: Quantification by an Enzyme–Linked Differential Antibody Immunosorbent Assay and Comparison with Alpha–2–Plasmin Inhibitor–Plasmin Complexes," *Blood*, 61:842–849 (May, 1983).
Cavarocchi, et al., "Evidence for complement activation by protamine–heparin interaction after cardiopulmonary bypass," *Surgery*, 98:525–531 (Sep.,1985).
Chenoweth, et al., "Complement Activation During Cardiopumonary Bypass," *N. Engl. J. Med.*,304(9):497–503 (Feb. 26, 1981).
Chenoweth, et al., "Demonstration of specific C5a receptor on intact human polymorphonuclear leukocytes," *Proc. Natl. Acad. Sci. USA*, 75(8):3943–3947 (Aug., 1978).
Clardy, "Complement Activation by Whole Endotoxin Is Blocked by a Monoclonal Antibody to Factor B," *Infect. Immun.*, 62(10):4539–4555 (Oct., 1994).
Dalmasso, et al., "Mechanism of Complement Activation in the Hyperacute Rejection of Porcine Organs Transplanted into Primate Recipients," *Am. J. Pathol.*, 140(5):1157–1166 (May, 1992).
Daoudaki, et al., "A 34–Amino Acid Peptide of the Third Component of Complement Mediates Properdin Binding," *J. Immunol.*, 140(5):1577–1580 (Mar. 1, 1988).
Eikelenboom, et al., "Complement activation in amyloid plaques in Alzheimer's dementia," *Virchows Arch. (Cell pathol.)* 56:259–262 (1989).

(List continued on next page.)

*Primary Examiner*—David Saunders
*Assistant Examiner*—Amy DeCloux
(74) *Attorney, Agent, or Firm*—McAndrews, Held & Malloy, Ltd.

(57) ABSTRACT

A process of inhibiting activation of complement via the alternative pathway, including inhibiting the formation of complement activation products via the alternative pathway, is provided.

14 Claims, 12 Drawing Sheets

OTHER PUBLICATIONS

Farries, et al., "Analysis of the interactions between properdin, the third component of complement (C3), and its physiological activation products," *Biochem. J.*, 252:47–54 (1988).

Finn, et al., "Interleukin-8 release and neutrophil degranulation after pediatric cardiopulmonary bypass," *J. Thorac. Cardiovasc. Surg.*, 105(2):234–241 (1993).

Fischel, et al., "Removal of IgM Anti–Endothelial Antibodies Results in Prolonged Cardiac Xenograft Survival," *Transplant Proc.*, 22(3):1077–1078 (Jun., 1990).

Fletcher, et al., "C5a–induced myocardial ischemia: role for CD18–dependent PMN localization and PMN–platelet interactions," *Am. J. Physiol.*, 265:H1750–H1761 (1993).

Foreman, et al., "C5a–induced Expression of P–selectin in Endothelial Cells," *J. Clin. Invest.*, 94:1147–1155 (Sep., 1994).

Fredrikson, et al. "Molecular Characterization of Properdin Deficiency Type III," *J. Immunol.* 157:3666–3671 (1996).

Fredrikson, et al., "New Procedure for the detection of complement deficiency by ELISA," *J. Immunol. Meth.*, 166:263–270 (1993).

Gelfand, et al., "Alternative Complement Pathway Activation Increases Mortality in a Model of Burn Injury in Mice," *J. Clin. Invest.*, 70:1170–1176 (1982).

Gelfand, et al., "Preferential Activation and Depletion of the Alternative Complement Pathway by Burn Injury," *Ann. Surg.*,198(1):58–62 (1983).

Gillinov, et al., "Complement Inhibition with Soluble Complement Receptor Type I in Cardiopulmonary Bypass," *Ann. Thorac. Surg.*, 55:619–624 (1993).

Gong, et al., "Tubing Loops as a Model for Cardiopulmonary Bypass circuits: Both the Biomaterial and the Blood–Gas Phase Interfaces Induce Complement Activation in an in Vitro Model," *J. Clin Immunol.*, 16(4):222–229 (1996).

Hack, et al., "Elevated Plasma Levels of the Anaphylatoxins C3a and C4a are Associated with a Fatal Outcome in Sepsis," *Am J. Med.*, 86:20–26 (Jan., 1989).

Hakim, et al., "Complement Activation and Hypersensitivity Reactions to Dialysis Membranes," *New Eng. J. Med.*, 311:878–882 (Oct. 4, 1984).

Haslam, etal., "Complement activation during cardiopulmonary bypass," *Anaesthesia*, 25(35):22–26 (1980).

Hattori, et al., "Complement Proteins C5b–9 Induce Secretion of High Molecular Weight Multimers of Endothelial von Willebrand Factor and Translocation of Granule Membrane Protein GMP–140," *J. Biol. Chem.*, 264(15):9053–9060 (May 25, 1989).

Hill, et al., "Soluble Complement Receptor Type 1 Ameliorates the Local and Remote Organ Injury After Intestinal Ischemia–Reperfusion in the Rat," *J. Immunol.*, 149(5):1723–1728 (Sep. 1, 1992).

Hsu, et al., "The Alternative Pathway Mediates Complement Activation in Reperfusion Injury," *Clin. Res.*, 41:233A (1993)

Hulett, et al., "Molecular Basis of Fc Receptor Funtion," *Adv. Immunol.*, 57:1–127 (1994).

Janeway, et al., "Immunobiology: the Immune System in Health and Disease," pp. 3:28–3:30. Garland Publishing, Inc., New York (1994).

Kaczorowski, et al., "Effect of Soluble Complement Receptor–1 on Neutrophil Accumulation After Traumatic Brain Injury in Rats," *J. Cereb. Blood Flow Metab.*, 15(5):860–864 (1995).

Kalli, et al., "Therapeutic uses of recombinant complement protein inhibitors," *Springer Semin Immunopathol.*, 15:417–431 (1994).

Kilgore, et al., "The complement system in myocardial ischaemia/reperfusion injury," *Cardiovascular Res.*, 28:437–444 (1994).

Kilpatrick, "Control of the Alternative Complement Pathway: Inhibition of Factor D," IBC's Second Annual Conference on Controlling the Complement System for Novel Drug Development, Conference Binder, (1996).

Kirklin, et al., "Complement and the damaging effects of cardiopulmonary bypass," *J. Thorac. Cardiovascu. Surg.*, 86:845–857 (1983).

Kohler et al., "Continuous cultures of fused cells secreting antibody of predefined specificity," *Nature*, 256:495–497 (1975).

Leventhal, et al., "Prolongation of Cardiac Xenograft Survival by Depletion of Complement," *Transplantation*, 55(4):857–866 (Apr., 1993).

Lindsay, et al., "Blockade of Complement Activation Prevents Local and Pulmonary Albumin Leak After Lower Torso Ischemia–Reperfusion," *Ann. Surg.*, 216:677–683 (1992).

Linington, et al., "The Role of Complement in the Pathogenesis of Experimental Allergic Encephalomyelitis," *Brain*,112:895–911 (1989).

Liszewski, et al., "The Complement System," *Fundamental Immunology*, Third Edition. Edited by W.E. Paul, Raven Press, Ltd. New York p. 917–939.

Mariani, et al., "A New Enzymatic Method to Obtain High–Yield F(ab)$_2$ Suitable for Clinical Use From Mouse IgG1," *Mol. Immunol.*,28(1/2):69–71 (1991).

Mollnes, et al., "Complement Activation in Rheumatoid Arthritis Evaluated by C3dg and the Terminal Complement Complex," *Arthritis and Rheumatism.*, 29(6);715–721 (1986).

Moore, "Therapeutic Regulation of the Complement System in Acute Injury States," *Advan. Immunol.*,56:267–299 (1994).

Moore, et al., "The Effects of Complement Activation During Cardiopulmonary Bypass," *Ann. Surg.*, 208(1):95–103 (1988).

Morgan, "Clinical complementology: recent progress and future trends," *Eur. J. Clinical Investig.*, 24:219–228.

Morgan, et al., "Complement deficiency and disease," *Immunology Today*, 12:301–306 (1991).

Morgan, et al., "Measurement of terminal complement complexes in rheumatoid arthritis," *Clin. Exp. Immunol.*, 73:473–478 (1988).

Morgan, et al., "Role of Complement in Inflammation and Injury in the Nervous System," *Exp. Clin. Immunogenet*, 14:19–23 (1997).

Maroko, et al., "Reduction by cobra Venom Factor of Mycardial Necrosis after Coronary Artery Occulusion," *J. Clin. Invest.*, 61:661–670 (1978).

Mulligan, et al., "Protective Effects of Soluble CRI in Complement– and Neutrophil–Mediated Tissue Injury," *J. Immunol.*, 148(5):1479–1485 (Mar. 1, 1992).

Mulligan, et al., "Requirement and Role of C5a in the Acute Lung Inflammatory Injury in Rats," *J. Clin. Invest.*, 98(2):503–512 (1996).

Mulligan, et al., "Role of Leukocyte Adhesion Molecules in Complement–Induced Lung Injury," *J. Immunol.*, 150(6):2401–2406 (Mar. 15, 1993).

Nakano, et al., "*Myasthenia gravis*: Quantitative immunocytochemical anslysis of lammatory cells and detection of complement membrane attack complex at the end–plate in 30 patients," *Neurology*, 43:1167–72 (Jun., 1993).

Nolan, et al., "Properdin," *Methods Enzymol.*, 223:35–47 (1993).

Pangburn, "Alternative Pathway of Complement," *Meth. In Enzymology*, 162:639–653 (1988).

Pangburn, et al., "The Alternative Pathway of Complement," *Springer Semin. Immunopathol.*, 7:163–192 (1984).

Pascual, et al., "Inhibition of complement alternative pathway in mice with Fab antibody to recombinant adipsin/factor D," *Eur. J. Immunol.*, 23:1389–1392 (1993).

Pemberton, et al., "Microvascular Effects of Complement Blockade with Soluble Recombinant CR1 on Ischemia/Reperfusion Injury of Skeletal Muscle," *J. Immunol.*, 150(11):5104–5113 (Jun. 1, 1993).

Platt, et al., "Immunopathology of Hyperacute Xenograft Rejection in a Swine–to–Primate Model," *Transplantation*, 52(2):214–230 (Aug., 1991).

Polhill, et al., "Kinetic Assessment of Alternative Complement Pathway Activity in a Hemolytic System," *J. Immunol.*, 121(1);363–370 (Jul., 1978).

Pruitt, et al., "The Effect of Soluble Complement Receptor Type 1 on Hyperacute Xenograft Rejection," *Transplantation*, 52(5):868–873 (Nov., 1991).

Ravtech, et al., "Fc Receptors," *Ann. Rev. Immunol.*, 9:457–492 (1991).

Rinder, et al., "Blockade of C5a and C5b–9 Generation Inhibits Leukocyte and Platelet Activation during Extracorporeal Circulation," *J. Clin. Invest.*, 96:1564–1572 (1995).

Rogers, et al., "Complement activation by β–amyloid in Alzheimer disease," *Transplantation Proc. Natl. Acad. Sci. USA*, 89:10016–10020 (Nov., 1992).

Roxvall, et al., "Anaphylatoxin Generation in Acute Pancreatitis," *J. Surg. Res.*, 47:138–143 (1989).

Roxvall, et al., "Anaphylatoxins and Terminal Complement Complexes in Pancreatitis," *Arch. Surg.*, 125:918–921 (Jul., 1990).

Rubin, et al., "Complement activation and white cell sequestration in postischemic skeletal muscle," *Am. J. Physiol.*, 259:H525–H531 (1990).

Salama, et al., "Deposition of Terminal C5b–9 Complement Complexes on Erythrocytes and Leukocytes during Cardiopulmonary Bypass," *N. Engl. J. Med.*, 318:408–414 (Feb. 18, 1988).

Sanders, et al., "Activated Terminal Complement in Cerebrospinal Fluid in Guillain–Barre Syndrome and Multiple Sclerosis," *J. Immunol.*, 136(12):4459 (Jun. 15, 1986).

Schafer, et al., "Deposition of the Terminal C5b–9 Complement Complex in Infarcted Areas of Human Myocardium," *J. Immunol.*, 137:1945–1949 (1986).

Schreiber, et al., "Initiation of the alternative pathway of complement: Recognition of activators by bound C3b and assembly of the entire pathway from six isolated proteins," *Proc. Natl. Acad. Sci. USA*, 75(8):3948–3952 (Aug., 1978).

Schwaeble, et al., "Properdin, a Positive Regulator of Complement Activation, Is Expressed in Human T Cell Lines and Peripheral Blood T Cells," *J. Immunol.*, 151(5):2521–2528 (Sep. 1, 1993).

Schwaeble, et al., "Expression of properdin in human monocytes," *Eur. J. Biochem.*, 219:759–764 (1994).

Schwaeble, et al., "Properdin, A Positive Regulator of Complement Activation, is Released from Secondary Granules of Stimulated Peripheral Blood Neutrophils," *Molec. Immunol.*, 33(Supp. 1):48–(1996).

Sissons et al., "Antibody–independent activation of the alternative complement pathway by measles virus–infected cells," *Proc. Natl. Acad. Sci. USA*, 77(1):559–562 (Jan., 1980).

Smith, III, et al., "Reduction of myocardial reperfusion injury with human soluble complement receptor type 1 (BRL 55730)" *Eur. J. Pharmac.*, 236:477–481 (1993).

Soderstrom, et al., "Bactericidal Activity for *Neisseria meningitidis* in Properdin–Deficient Sera," *J. Infect. Dis*, 156(1):107–112 (Jul., 1987).

Solomkin, et al., "Complement activation and clearance in acute illness and injury: Evidence for C5a as a cell–directed mediator of the adult respiratory distress syndrome in man," *Surgery*, 97(6):668–678 (1985).

Solomkin, et al., "Regulation of Neutrophil Migratory Function in Burn Injury by Complement Activation Products," *Ann. Surg.*, 200(6):742–746 (1984).

Steinberg, et al., "Cytokine and complement levels in patients undergoing cardiopulmonary bypass," *J. Thorac. Cardiovasc. Surg.*, 106(6):1008–1016 (1993).

Stevens, et al., "Effects of Anti–C5a Antibodies on the Adult Respiratory Distress Syndrome in Septic Primates," *J. Clin. Invest.*, 77:1812–1816 (1986).

Tosi, et al., "A Rapid, Specific Assay for Superoxide Release from Phagocytes in Small Volumes of Whole Blood," *Am. J. Clin. Pathol.*, 97(4):566–573 (1992).

Vasthare, et al., "Involvement of the complement System in Cerebral Ischemic and Reperfusion Injury," *FASEB J.*, 7:A424 (1993).

Velthius, et al., "Specific Complement Inhibition With Heparin–Coated Extracorporeal Circuits," *Ann. Thorac. Surg.*, 61:1153–1157 (1996).

Volanakis, et al., "Purification and Properties of Human Factor D," *Methods in Enzymol.*, 223:82–97 (1993).

Wachtfogel, et al., "Formation of C1–C1–Inhibitor, Kallikrein–C1–Inhibitor, and Plasmina–$\alpha_2$–Plasmin–Inhibitor Complexes During Cardiopulmonary Bypass," *Blood*, 73(2):468–471 (Feb., 1989).

Wakabayashi, et al., "*Staphylococcus Epidermidis* Induces Complement Activation, Tumor Necrosis Factor and Interleukin–1, a Shock–like State and Tissue Injury in Rabbits Without Endotoxemia," *J. Clin. Invest.*, 87:1925–1935 (Jun., 1991).

Wan, et al., "Inflammatory Response to Cardipulmonary Bypass," *Chest*, 112:676–692 (1997).

Wang, et al., "Anti–C5 monoclonal antibody therapy prevents collagen–induced arthritis and ameliorates established disease," *Proc. Natl. Acad. Sci. USA*, 92:8955–8959 (Sep., 1995).

Wang. et al., "Amelioration of lupus–like autoimmune disease in NZB/W F1 mice after treatment with a blocking monoclonal antibody specific for complement component C5," *Proc. Natl. Acad. Sci. USA*, 93:8563–8568 (Aug., 1996).

Watson, et al., "Genetic Susceptibility to Murine Collagen II Autoimmune Arthritis," *J.Exp. Med.*, 162:1878–1891 (Dec., 1985).

Weisman, et al., "Soluble Human Complement Receptor Type 1: In Vivo Inhibitor of Complement Suppressing Post–Ischemic Myocardial Inflammation and Necrosis," *Science*, 249:146–151 (Jul. 13, 1990).

White, et al., "Human Adipsin Is Identical to Complement Factor D and Is Expressed at High Levels in Adipose Tissue," *J. Biol. Chem.*, 267(13):9210–9213 (May 5, 1992).

Whitty, "A Sheep in Wolf's Clothing: The Activation Mechanism of Factor D," IBC's Second Annual Conference on Controlling the Complement System for Novel Drug Development, Conference Binder, 4 pages (1996).

Wurzner, et al., "Inhibition of Terminal Complement Complex Formation and Cell Lysis by Monoclonal Antobides," *Complement Inflamm*, 8:328–340 (1991).

Xia, et al., "Prolongation of Guinea Pig Cardiac Xenograft Survival in Rats by Soluble Human Complement Receptor Type 1," *Transplant. Proc.*, 24(2):479–480 (Apr., 1992).

Zilow, et al., "Complement activation and the prognostic value of C3a in patients at risk of adult respiratory distrass syndrome," *Clin. Exp. Immunol.*, 79:151–157 (1990).

* cited by examiner

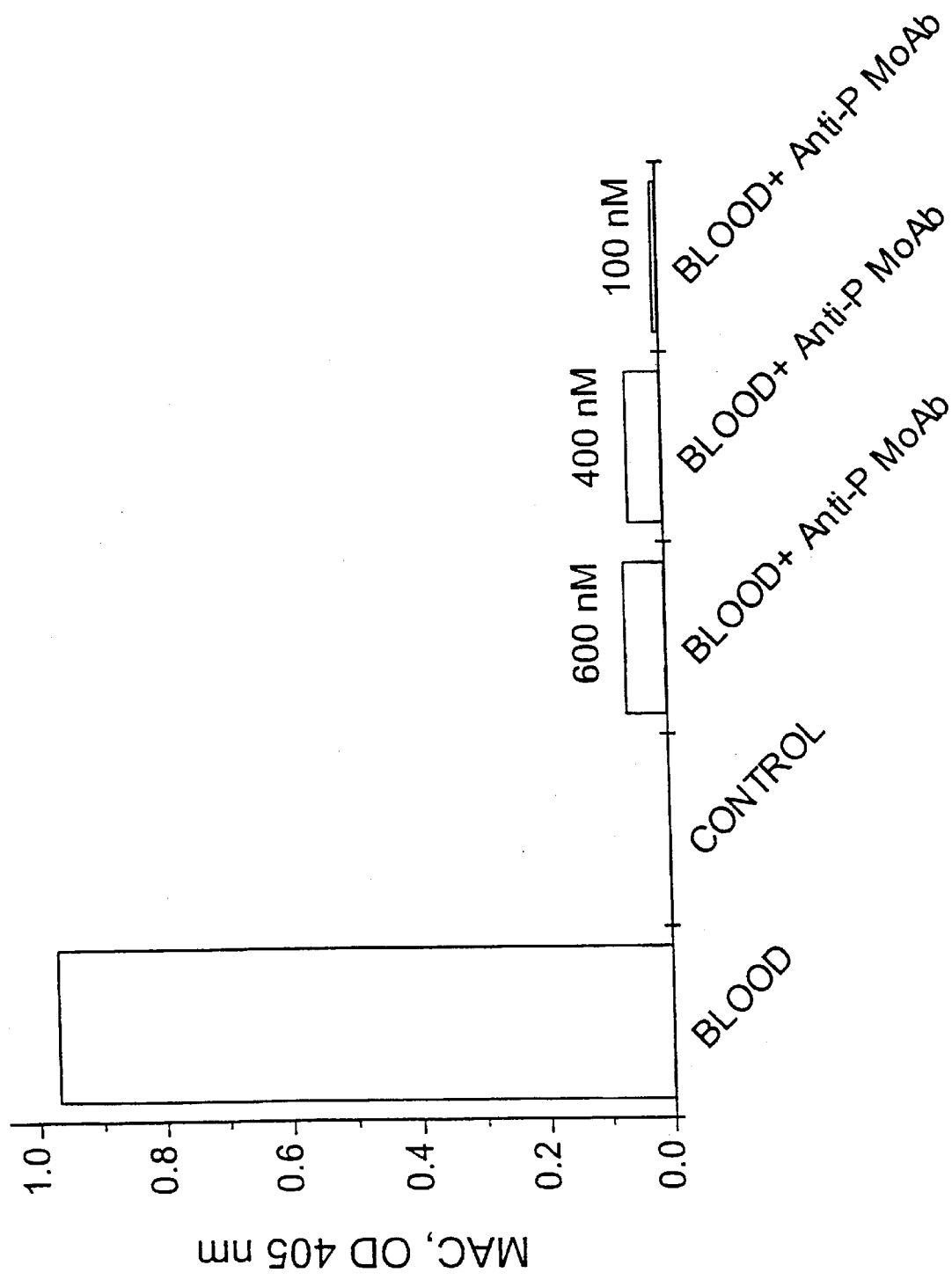

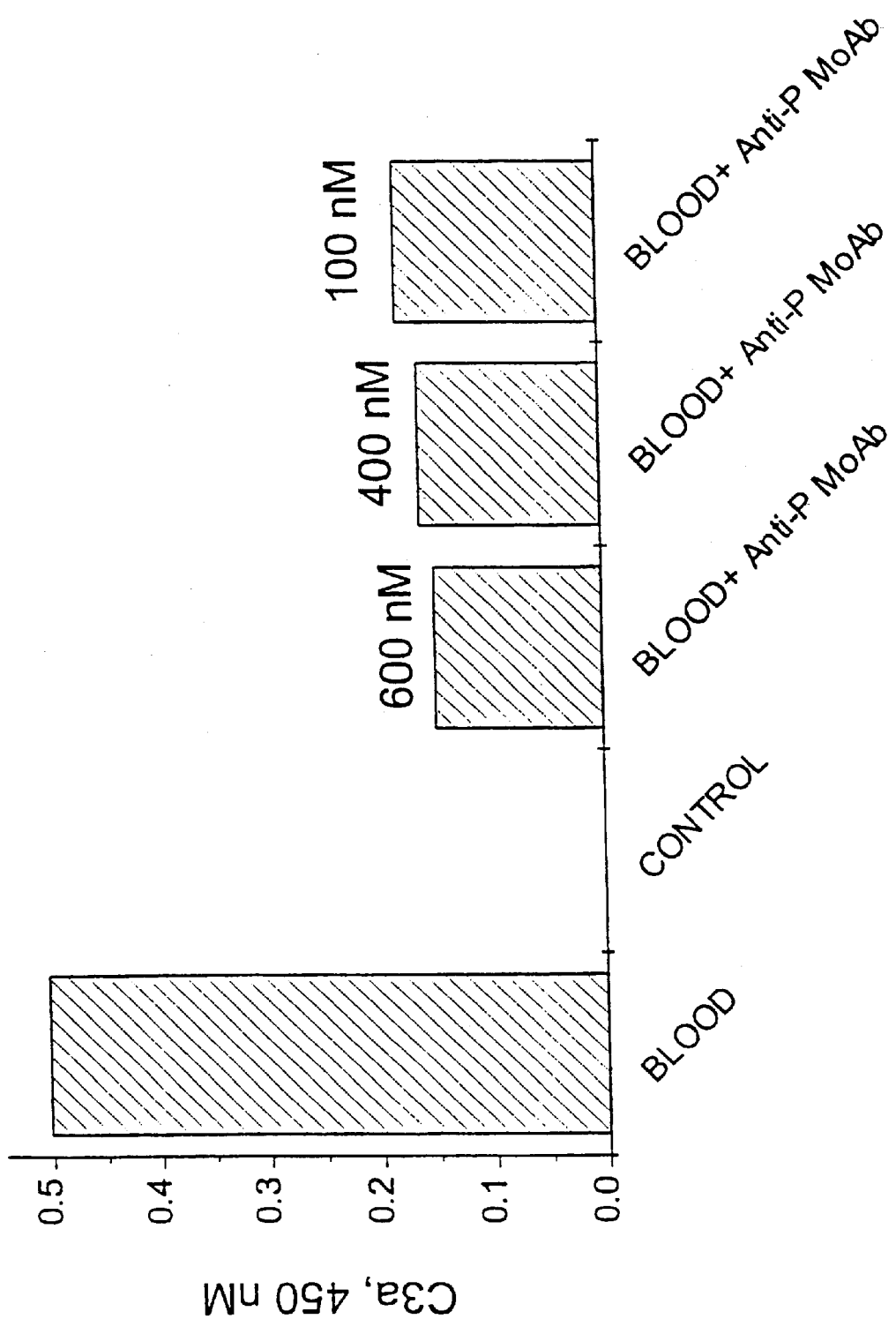

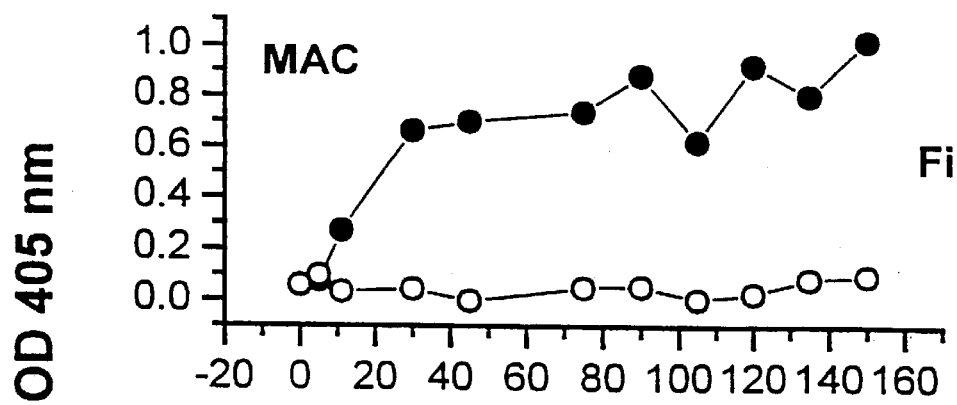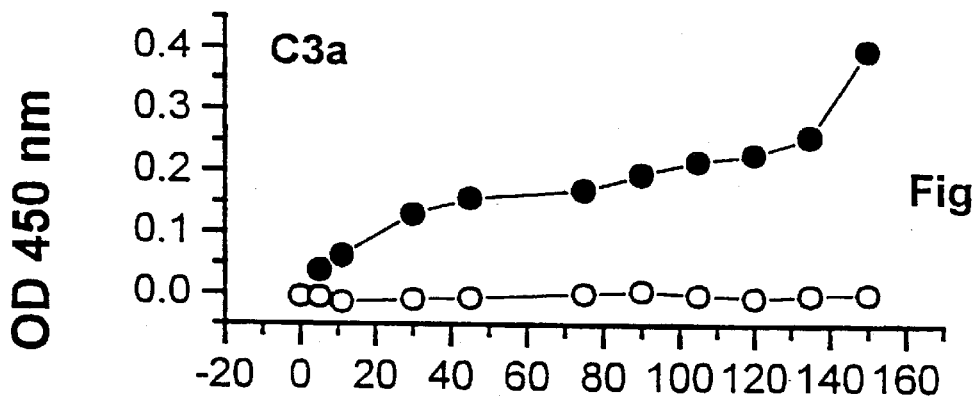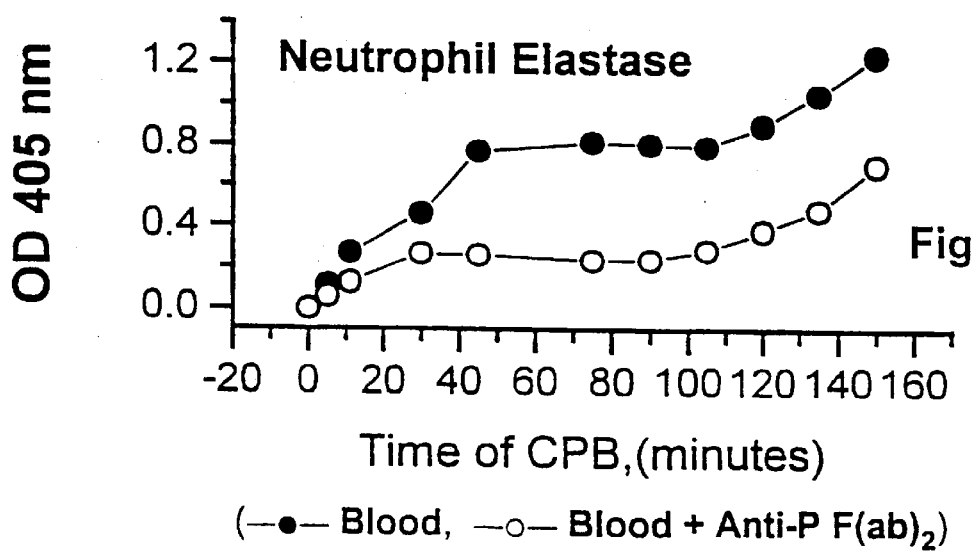

PROCESS FOR INHIBITING COMPLEMENT ACTIVATION VIA THE ALTERNATIVE PATHWAY

This application is a continuation-in-part of U.S. application Ser. No. 08/918,349 filed Aug. 26, 1997, now abandoned, incorporated herein by reference.

TECHNICAL FIELD OF THE INVENTION

The field of this invention is complement activation. More particularly, the present invention pertains to a process for inhibiting complement activation via the alternative pathway, including for inhibiting the formation (i.e., generation or production) of complement activation products via the alternative pathway.

BACKGROUND OF THE INVENTION

The complement system provides an early acting mechanism to initiate and amplify the inflammatory response to microbial infection and other acute insults. (Liszewski, M. K. and J. P. Atkinson, 1993, In *Fundamental Immunology*, Third Edition. Edited by W. E. Paul. Raven Press, Ltd. New York). While complement activation provides a valuable first-line defense against potential pathogens, the activities of complement that promote a protective inflammatory response can also represent a potential threat to the host. (Kalli, K. R., P. Hsu, and D. T. Fearon, 1994, *Springer Semin Immunopathol.* 15:417–431; Morgan, B. P., Eur. *J. Clinical Investig.* 24:219–228). For example, C3 and C5 proteolytic products recruit and activate neutrophils. These activated cells are indiscriminate in their release of destructive enzymes and may cause organ damage. In addition, complement activation may cause the deposition of lytic complement components on nearby host cells as well as on microbial targets, resulting in host cell lysis. The growing recognition of the importance of complement-mediated tissue injury in a variety of disease states underscores the need for effective complement inhibitory drugs. No approved drugs that inhibit complement damage currently exist.

Complement can be activated through either of two distinct enzymatic cascades, referred to as the classical and alternative pathways. (Liszewski, M. K. and J. P. Atkinson, 1993, In *Fundamental Immunology*, Third Edition. Edited by W. E. Paul. Raven Press, Ltd. New York). The classical pathway is usually triggered by antibody bound to a foreign particle and thus requires prior exposure to that particle for the generation of specific antibody. There are four plasma proteins specifically involved in the classical pathway: C1, C2, C4 and C3. The interaction of C1 with the Fc regions of IgG or IgM in immune complexes activates a C1 protease that can cleave plasma protein C4, resulting in the C4a and C4b fragments. C4b can bind another plasma protein, C2. The resulting species, C4b2, is cleaved by the C1 protease to form the classical pathway C3 convertase, C4b2a. Addition of the C3 cleavage product, C3b, to C3 convertase leads to the formation of the classical pathway C5 convertase, C4b2a3b.

In contrast to the classical pathway, the alternative pathway is spontaneously triggered by foreign or other abnormal surfaces (bacteria, yeast, virally infected cells, or damaged tissue) and is therefore capable of an immediate response to an invading organism (Liszewski, M. K. and J. P. Atkinson, 1993, In *Fundamental Immunology*, Third Edition. Edited by W. E. Paul. Raven Press, Ltd. New York). There are four plasma proteins directly involved in the alternative pathway: C3, factors B and D, and properdin (also called factor P).

The initial interaction that triggers the alternative pathway is not completely understood. However, it is thought that spontaneously activated C3 [sometimes called C3($H_2O$)] binds factor B, which is then cleaved by factor D to form a complex [C3($H_2O$)Bb] with C3 convertase activity. The resulting convertase proteolytically modifies C3, producing the C3b fragment, which can covalently attach to the target and then interact with factors B and D and form the alternative pathway C3 convertase, C3bBb. The alternative pathway C3 convertase is stabilized by the binding of properdin. Properdin extends its half-life six-to ten-fold (Liszewski, M. K. and J. P. Atkinson, 1993, In *Fundamental Immunology*, Third Edition. Edited by W. E. Paul. Raven Press, Ltd. New York). However, properdin binding is not required to form a functioning alternative pathway C3 convertase (Schreiber, R. D., M. K. Pangburn, P. H. Lesavre and H. J. Muller-Eberhard, 1978, Proc. *Natl. Acad. Sci. USA* 75:3948–3952; Sissons, J. G., M. B. Oldstone and R. D. Schreiber, 1980, *Proc. Natl. Acad. Sci. USA* 77:559–562). Since the substrate for the alternative pathway C3 convertase is C3, C3 is therefore both a component and a product of the reaction. As the C3 convertase generates increasing amounts of C3b, an amplification loop is established (Liszewski, M. K. and J. P. Atkinson, 1993, In *Fundamental Immunology*, Third Edition. Edited by W. E. Paul. Raven Press, Ltd. New York). Inasmuch as the classical pathway also may generate C3b, that C3b can bind factor B and thereby engage the alternative pathway. This allows more C3b to deposit on a target. For example, as described above, the binding of antibody to antigen initiates the classical pathway. If antibodies latch on to bacteria, the classical pathway generates C3b, which couples to target pathogens. However, it has been suggested that from 10% to 90% of the subsequent C3b deposited may come from the alternative pathway (Liszewski, M. K. and J. P. Atkinson, 1993, In *Fundamental Immunology*, Third Edition. Edited by W. E. Paul. Raven Press, Ltd. New York). The actual contribution of the alternative pathway to the formation of additional C3b subsequent to classical pathway initiation has not been clearly quantified and thus remains unknown. Addition of C3b to the C3 convertase leads to the formation of the alternative pathway C5 convertase, C3bBbC3b.

Both the classical and alternative pathways converge at C5, which is cleaved to form products with multiple proinflammatory effects. The converged pathway has been referred to as the terminal complement pathway. C5 a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites and reactive oxygen species. C5 cleavage leads to the formation of C5b-9, also known as the membrane attack complex (MAC). There is now strong evidence that MAC may play an important role in inflammation in addition to its role as a lytic pore-forming complex (Liszewski, M. K. and J. P. Atkinson, 1993, In *Fundamental Immunology*, Third Edition. Edited by W. E. Paul. Raven Press, Ltd. New York).

Complement activation has been implicated as contributing to a variety of disease states and conditions, as well as complications from a variety of medical procedures (see references cited infra) such as: myocardial infarction; ischemia/reperfusion injury; stroke; acute respiratory distress syndrome (ARDS); sepsis; burn injury; complications resulting from extracorporeal circulation (ECC) including most commonly from cardiopulmonary bypass (CPB) but also from hemodialysis or plasmapheresis or plateletpheresis or leukophereses or extracorporeal membrane oxygenation (ECMO) or heparin-induced extracorporeal LDL precipitation (HELP); use of radiographic contrast media; transplant rejection; rheumatoid arthritis; multiple sclerosis; myasthenia gravis; pancreatitis; and Alzheimer's disease. There is still no effective complement inhibitory drug available for routine clinical use despite the significant medical need for such agents.

The ability to specifically inhibit only the pathway causing a particular pathology without completely shutting down the immune defense capabilities of complement would be highly desirable. Based upon the available clinical data, it appears that in most acute injury settings, complement activation is mediated predominantly by the alternative pathway (Moore, F. D. 1994, *Advan. Immunol.* 56:267–299; Bjornson, A. B., S. Bjornson and W. A. Altemeier, 1981 *Ann. Surg.* 194:224–231: Gelfand, J. A., M. Donelan, and J. F. Burke, 1983, Ann. Surg. 198:58–62). These findings suggest that it would be advantageous to specifically inhibit alternative pathway-mediated tissue damage in a variety of acute injury settings, for example, in myocardial infarction, ARDS, reperfusion injury, stroke, thermal burns, and post-cardiopulmonary bypass inflammation. This would leave the classical pathway intact to handle immune complex processing and to aid in host defense against infection. As essential components of the alternative pathway, factors B and D are attractive targets for specific inhibition of the alternative pathway. Because of its non-essential role, properdin, however, would not be expected to be a suitable target for such intervention.

BRIEF SUMMARY OF THE INVENTION

The present invention provides a process of inhibiting alternative pathway complement activation. The process includes the step of inhibiting properdininduced stabilization of C3 convertase. Properdin-induced stabilization of C3 convertase is inhibited by inhibiting the binding of properdin to C3b or C3bBb. The binding of properdin to C3b is inhibited by exposing properdin to an effective amount of an antibody against properdin.

A process of the present invention is particularly useful in inhibiting complement activation via the alternative pathway in vivo in subjects, including humans, suffering from an acute or chronic pathological injury such as, but not limited to, myocardial infarction, acute respiratory distress syndrome, burn injury, stroke, multiple sclerosis, rheumatoid arthritis, Alzheimer's disease or ischemia/reperfusion injury. In vivo inhibition of complement activation is accomplished by administering the anti-properdin antibody to the subject. Pharmaceutical compositions containing anti-properdin antibodies are also provided.

The present invention provides, in one aspect, a process of inhibiting the adverse effects of alternative complement pathway activation in a subject by administering to the subject an amount of an anti-properdin agent effective to selectively inhibit formation (i.e., generation or production) of a complement activation product via the alternative complement pathway. Formation of such alternative pathway-dependent activation products refers to the generation or production of such products by complement activation, which products when generated or produced can be detected and include alternative pathway-dependent C3a, C5a, and/or C5b-9 (MAC) products. An anti-properdin agent according to the invention blocks properdin as described herein and selectively inhibits the formation of alternative complement pathway activation products. Such agents include an anti-properdin antibody, an antigen-binding fragment of an anti-properdin antibody, and a properdin-derived peptide. Preferably, the anti-properdin agent does not substantially activate Fcγ receptors and/or the classical complement pathway.

The present invention provides, in another aspect, a process for inhibiting the adverse effects of classical complement pathway activation in a subject in which the classical complement pathway is initiated by administering to the subject an amount of an anti-properdin agent effective to selectively inhibit formation of an alternative complement pathway activation product (e.g., alternative pathway-dependent C3a, C5a, MAC).

The present invention provides, in another aspect, a process for inhibiting the adverse effects of classical complement pathway activation in a subject in which the classical complement pathway is initiated by administering to the subject an amount of an agent that inhibits the alternative pathway C3 convertase effective to selectively inhibit formation of a complement activation product via the alternative complement pathway (e.g. alternative pathway-dependent C3a, C5a, MAC).

The present invention, in another aspect, provides a process for performing a medical procedure on a subject comprising: (a) passing circulating blood from a blood vessel of the subject, through a conduit and back to a blood vessel of the subject, the conduit having a luminal surface comprising a material capable of causing at least one of complement activation, platelet activation, leukocyte activation, or platelet-leukocyte adhesion in the subject's blood; and (b) introducing an anti-properdin agent into the subject's bloodstream in an amount effective to reduce at least one of complement activation, platelet activation, leukocyte activation, or platelet-leukocyte adhesion resulting from passage of the circulating blood through the conduit, wherein step (a) occurs before and/or during and/or after step (b). Preferably, the anti-properdin agent reduces the alternative pathway-dependent conversion of complement component C3 into complement components C3a and C3b, and/or the alternative pathway-dependent formation of C5b-C9, and/or the alternative pathway-dependent leukocyte activation. Medical procedures including therapeutic procedures according to the invention include extracorporeal circulation procedures, including for example, cardiopulmonary bypass (CPB) procedures.

The present invention provides, in another aspect, an article of manufacture comprising packaging material and a pharmaceutical agent (i.e., pharmaceutical composition) contained within the packaging material, wherein: (a) the pharmaceutical agent comprises an anti-properdin agent, the anti-properdin agent being effective for reducing at least one of complement activation, platelet activation, leukocyte activation, or platelet adhesion caused by passage of circulating blood from a blood vessel of a subject, through a conduit, and back to a blood vessel of the subject, the conduit having a luminal surface comprising a material capable of causing at least one of complement activation, platelet activation, leukocyte activation, or platelet-leukocyte adhesion in the subject's blood; and (b) the packaging material comprises a label which indicates that the pharmaceutical agent is for use in association with an extracorporeal circulation procedure. Articles of manufacture according to the invention include labels that indicate that the anti-properdin agents are for use in association with a cardiopulmonary bypass procedure.

The invention provides a use of an anti-properdin agent in the preparation of a medicament for selectively inhibiting formation of complement activation products via the alternative complement pathway in a subject in need thereof. Also provided is a use of an anti-properdin agent in the preparation of a medicament for selectively inhibiting formation of complement activation products via the alternative complement pathway in a subject in which the classical complement pathway is initiated. Additionally provided is a use of an alternative pathway C3 convertase-inhibiting agent in the preparation of a medicament for selectively inhibiting formation of complement activation products via the alternative complement pathway in a subject in which the classical complement pathway is initiated.

BRIEF DESCRIPTION OF THE DRAWINGS

In the drawings, which form a portion of the specification:

FIG. 7 shows the inhibition of the formation of alternative complement pathway activation products, including C3a and MAC, using an anti-properdin monoclonal antibody in a tubing loop model of cardiopulmonary bypass (CPB).

FIG. 11 shows the inhibition of the formation of alternative pathway-dependent complement and leukocyte activation products, including inhibition of C3a, MAC or elastase-antitrypsin complex product formation, using an anti-properdin agent in an ex vivo model of cardiopulmonary bypass (CPB).

DETAILED DESCRIPTION OF THE INVENTION

I. The Invention

Figure 1:
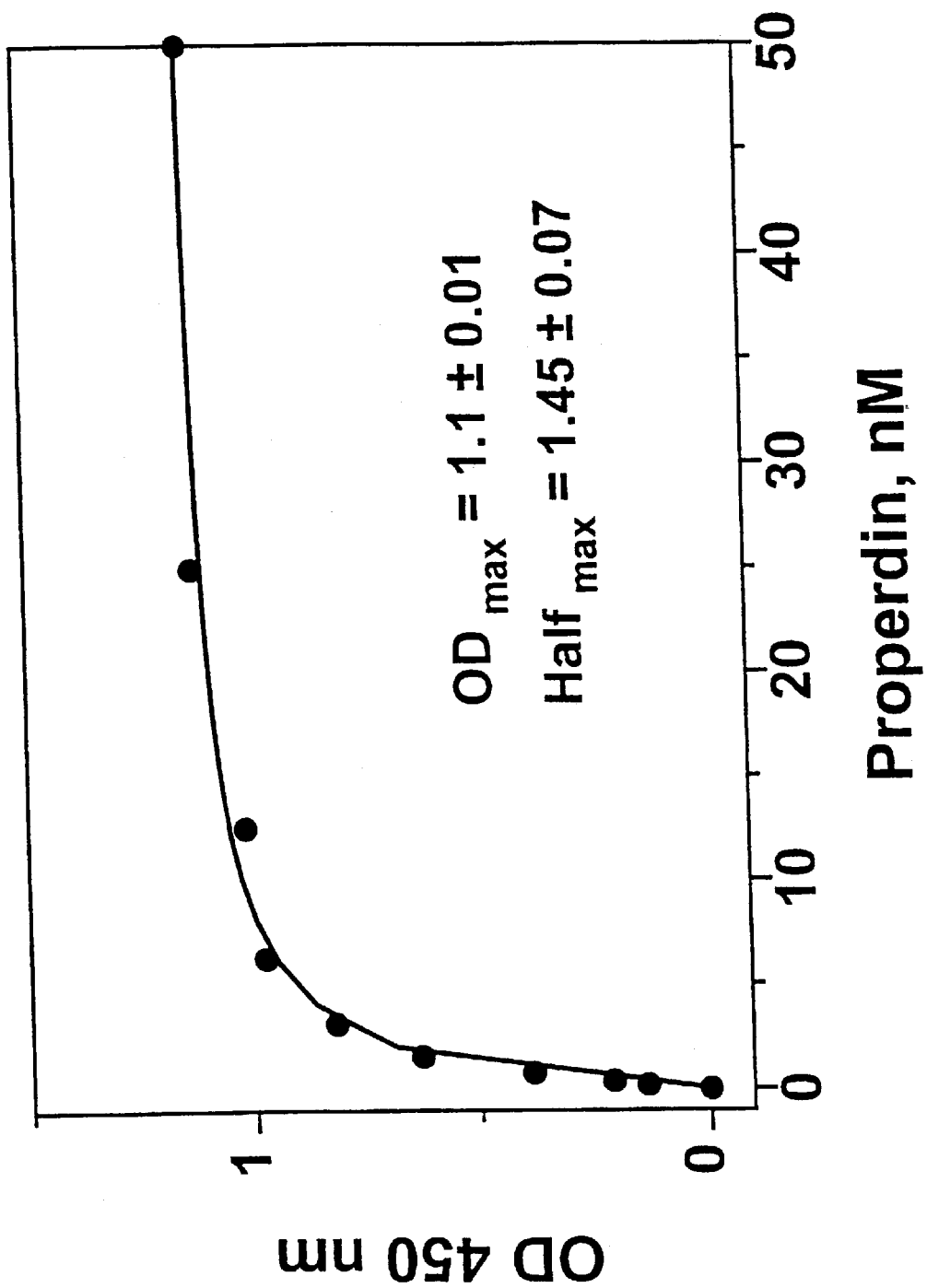
FIG. 1 shows binding of human properdin to C3b.
Figure 2:
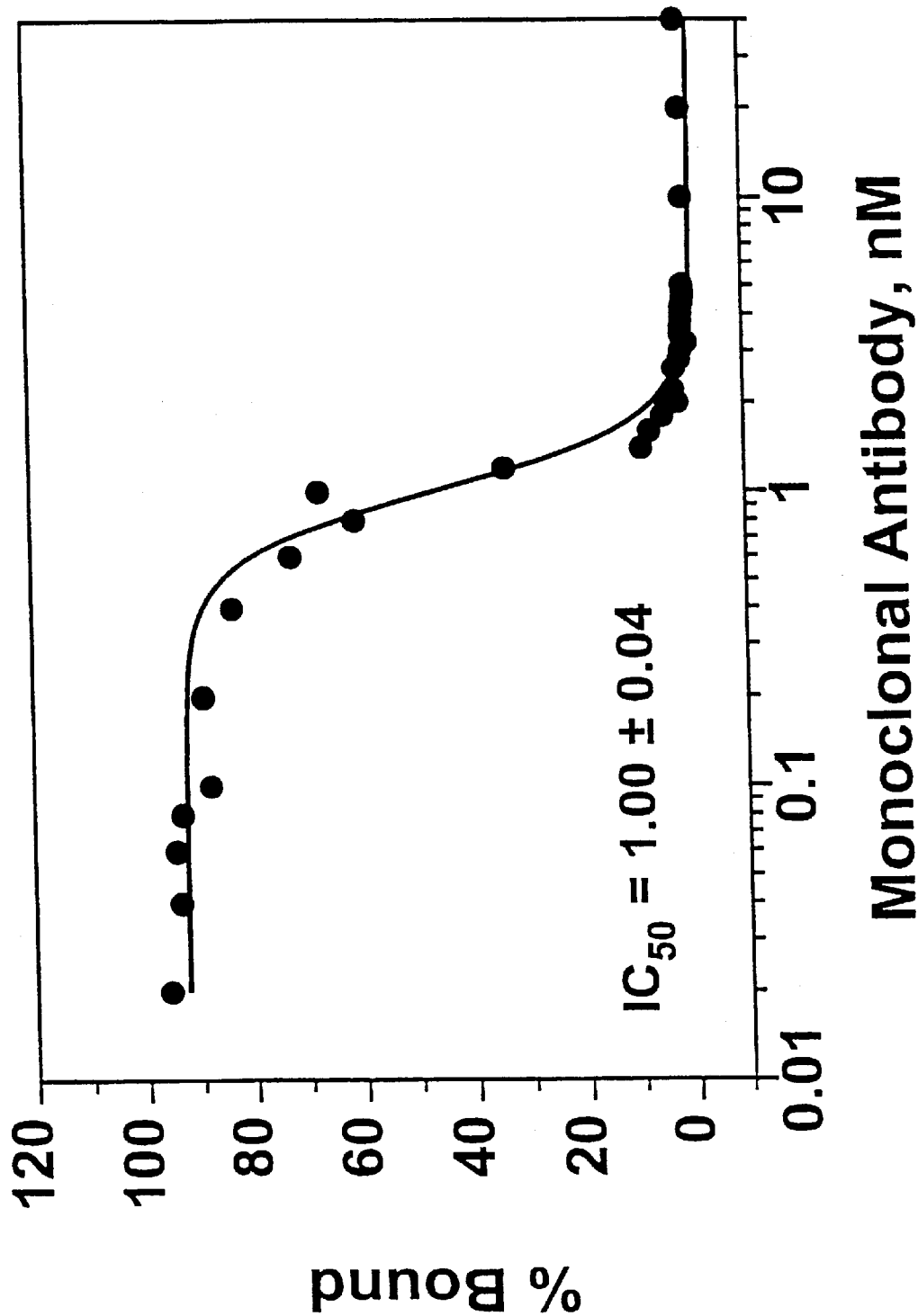
FIG. 2 shows the dose-dependent inhibition of properdin binding to C3b using an anti-properdin monoclonal antibody.
Figure 3:
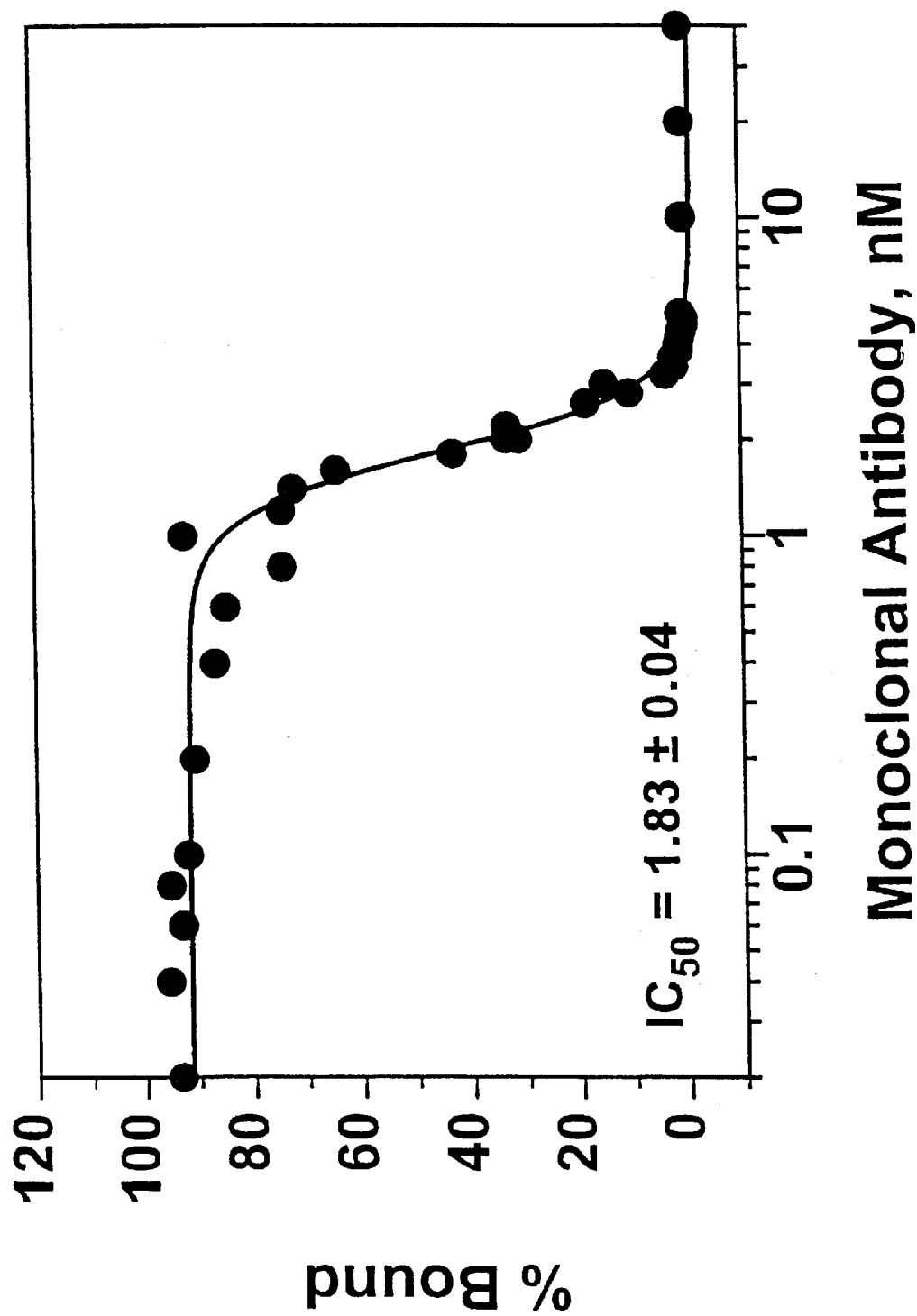
FIG. 3 shows the dose-dependent inhibition of properdin binding to C3bBb using an anti-properdin monoclonal antibody.

Properdin is one of three unique plasma proteins that are directly involved in the alternative pathway. Together with factor D and factor B, all three are potential targets for the development of therapeutic agents to inhibit the alternative pathway. As set forth below, properdin is shown for the first time herein to be a suitable target for a process of inhibiting complement activation via the alternative pathway. Properdin is also shown for the first time herein to be a suitable target even when the classical complement pathway has been initiated.

Factor D is a serine proteinase with only a single known natural substrate: factor B bound to C3b (Volanakis, J.E., S. R. Barnum, and J. M. Kilpatrick, 1993, *Methods in Enzymol.* 223:82–97). The serum concentration of factor D, 2 μg/rnl, is the lowest of any complement protein (Liszewski, M. K. and J. P. Atkinson, 1993, In *Fundamental Immunology*, Third Edition. Edited by W. E. Paul. Raven Press, Ltd. New York). Factor D is known to be the rate limiting enzyme for the alternative pathway and therefore a suitable target for therapeutic methods of inhibition complement activation via the alternative pathway. We believe, however, there are several reasons why inhibitors of factor D may not be ideal therapeutic agents for inhibiting complement activation. Firstly, serine proteinases are also critically involved in the coagulation and fibrinolytic systems, and it has proven difficult to identify specific inhibitors of factor D (Kilpatrick, J. M., 1996, IBC's Second Annual Conference on Controlling the Complement System for Novel Drug Development, Conference Binder; Whitty, A., 1996, IBC's Second Annual Conference on Controlling the Complement System for Novel Drug Development, Conference Binder). Secondly, factor D is a small protein (24.4 kDa) and is rapidly reabsorbed and catabolized by the kidney with a fractional catabolic rate of 60% per hour. The steady state serum concentration of factor D is maintained by a correspondingly high rate of synthesis. Therefore, it may be difficult to inhibit factor D activity in patient serum for prolonged periods without complicated drug dosing regimes. Thirdly, factor D is synthesized by adipocytes and there is evidence from studies with genetically obese mice that factor D may have a regulatory role in fat metabolism (White, R. T., D. Damm, N. Hancock, B. S. Rosen, B. B. Lowell, P. Usher, J. S. Flier, and B. M. Speigelman., 1992, *J. Biol. Chem.* 267:9210–9213). Therefore, inhibition of factor D may have detrimental secondary effects on patients that are not directly related to complement inhibition.

Factor B plays a key role in the alternative pathway since it provides the catalytic subunit, Bb, for the C3 convertase, C3bBb (Liszewski, M. K. and J. P. Atkinson, 1993, In *Fundamental Immunology*, Third Edition. Edited by W. E. Paul. Raven Press, Ltd. New York). Therefore, factor B also would appear to be another suitable target for therapeutic methods of inhibiting complement activation via the alternative pathway. Alone, factor B is a zymogen with no known catalytic activity, but after binding C3b, the factor B serine proteinase can be activated by cleavage by factor D. Based on this, it should be possible to develop specific inhibitors of factor Bb catalytic activity as therapeutic agents to inhibit the alternative pathway. However, similar to the experience with factor D, it has proven difficult to identify inhibitors of factor Bb proteinase activity that do not also inhibit serine proteinases involved in blood coagulation hemostasis (Whitty, A., 1996, IBC's Second Annual Conference on Controlling the Complement System for Novel Drug Development, Conference Binder). In any case, we believe factor B is probably not the best target for the development of therapeutic agents to inhibit the alternative pathway. Factor B is an abundant serum protein (~210 μg/ml) (Clardy, C. W., 1994, *Infect. Immun.* 62:4539–4555; Liszewski, M. K. and J. P. Atkinson, 1993, In *Fundamental Immunology*, Third Edition. Edited by W. E. Paul. Raven Press, Ltd. New York) and it would probably require a correspondingly high concentration of an inhibitor of factor B to effectively block activation of the alternative pathway. Monoclonal antibodies to human factor B, however, have been prepared and tested for their in vitro ability to block alternative complement pathway activation by endotoxin (LPS) (Clardy, C. W. 1994, *Infect Immun.* 62:4539–4555). One of the four monoclonal anti-factor B antibodies tested was able to effectively block alternative pathway activation. The other three antibodies tested failed to block despite having affinities that were similar to the blocking antibody. In three other studies of anti-factor B monoclonal antibodies that were cited by Clardy, et al., supra (1994), two monoclonals increased factor B activity by stabilizing the alternative pathway convertase, one increased factor B activity by enhancing binding of B to C3b, three decreased factor B activity by destabilizing the convertase and two decreased factor B activity by blocking binding of factor B to C3b.

Properdin plays a role in the regulation of the alternative pathway by virtue of its ability to bind and stabilize the inherently labile C3 and C5 convertase complexes (C3bBb and C3bBbC3b) (Nolan, K. F. and K. B. M. Reid, 1993, *Methods Enzymol.* 223:35–47), although the exact mechanism of C3 convertase stabilization is unknown (Daoudaki, M. E., J. D. Becherer and J. D. Lambris, 1988. *J. Immunol.* 140:1577–1580). Binding of properdin to these complexes may result in a decreased rate of dissociation of the Bb catalytic subunit and may also protect the complexes from degradation by the negative regulatory proteins, factors I and H. However, properdin is not required for functional C3 convertase activity (Schreiber, R. D., M. K. Pangburn, P. H. Lesavre and H. J. Muller-Eberhard, 1978, *Proc. Natl. Acad. Sci. USA* 75:3948–3952; Sissons, J. G., M. B. Oldstone and R. D. Schreiber, 1980, *Proc. Natl. Acad. Sci. USA* 77:559–562; Pangburn, M. K. and H. J. Muller-Eberhard, 1984, *Springer Semin. Immunopathol.* 7:163–192). The concentration of properdin in normal human plasma was determined to be 4.3–5.7 $\mu$g/nil, making it one of the least abundant complement proteins (Nolan, K. F. and K. B. M. Reid, 1993, *Methods Enzmol.* 223:35–47). In early studies, the plasma concentration of properdin was reported to be in the 20–25 mg/ml range; however, this estimate was based on an incorrect molar extinction coefficient for the protein. It is now known that the true plasma concentration of properdin is significantly lower (Nolan, K. F. and K. B. M. Reid, 1993, *Methods Enzymol.* 223:35–47). Human monocytes, neutrophils and T lymphocytes synthesize properdin (Schwaeble, W., W. G. Dippold, M. K. Schafer, H. Pohla, D. Jones, B. Luttig, E. Weihe, H. P. Huemer, M. P. Dierich, and K. B. M. Reid, 1993, *J. Immunol.* 151:2521–2528; Schwaeble, W., U. Wirthmuller, B. Dewald, M. Thelen, M. K. Schafer, P. Eggelton, K. Whaley, and K. B. M. Reid, 1996, *Molec. Immunol.* 33(1):48; Schwaeble, W., H. P. Huemer, J. Most, M. P. Dierich, M. Strobel, C. Claus, K. B. M. Redi and H. W. Ziegler-Heitbrock, 1994, J. Eur. Biochem. 219:759–764). Unlike most other complement proteins, properdin does not appear to be synthesized by the liver. Properdin is stored in granules of human neutrophils and physiologically-relevant levels of TNF, Il–8, FMLP and C5a induce its rapid secretion (Schwaeble, W., U. Wirthmuller, B. Dewald, M. Thelen, M. K. Schafer, P. Eggelton, K. Whaley, and K. B. M. Reid, 1996, *Molec. Immunol.* 33(1):48). In a human monocyte cell line, TNF and IL-1 enhanced both the abundance of properdin mRNA as well as secretion of the protein (Schwaeble, W., H. P. Huemer, J. Most, M. P. Dierich, M. Strobel, C. Claus, K. B. M. Redi and H. W. Ziegler-Heitbrock, 1994, *J. Eur. Biochem.* 219:759–764).

According to the present invention, of the three complement proteins that are uniquely involved in the alternative pathway, properdin is the most attractive target for development of a pathway-specific complement inhibitor to treat acute inflammatory disorders. As demonstrated hereinafter, an anti-properdin antibody that prevents binding of properdin to C3 convertase totally inhibits activation of the alternative pathway. Therefore, as described for the first time herein, properdin is required for normal activation of the alternative pathway. Because properdin is demonstrated herein to play a central role in complement activation, including in conditions involving initiation of the classical complement pathway, anti-properdin agents may be screened and selected that are unexpectedly effective in processes of selectively and potently inhibiting alternative complement pathway activation, including processes for inhibiting the formation of complement activation products via the alternative pathway.

II. Process of Inhibiting Alternative Pathway Activation of Complement

In one aspect, a process of the present invention provides for inhibition of complement activation via the alternative pathway, including for inhibiting the formation of complement activation products via the alternative pathway (e.g., MAC formation).

It is not well understood how properdin interacts with C3 convertase, although the primary binding specificity of properdin has been shown to be directed towards C3b (Nolan, K. F. and K. B. M. Reid, 1993, *Methods Enzymol.* 223:35–47). The properdin binding site on C3b has been localized to residues 1402–1435 in the alpha chain of C3, as judged by peptide inhibition studies (Daoudaki, M. E., J. D. Becherer and J. D. Lambris, 1988. *J. Immunol.* 140:1577–1580). The analysis of overlapping peptides indicates that the site could be further refined to residues 1424–1432 (Alzenz, J., J. D. Becherer, I. Esparza, M. E. Daoudaki, D. Avita, S. Oppermann, and J. D. Lambris, 1989, *Complement Inflamm.* 6:307–314). There is also evidence that properdin binds to factor B and this interaction appears to take place through sites on both the Ba and Bb portions of the molecule. Although properdin binds cell-bound C3b, the binding is significantly enhanced with cell-bound C3bBb, suggesting that binding sites of both C3b and Bb may contribute to the interaction of properdin with the convertase complex (Farries, T. C., P. J. Lachmann, and R. A. Harrison, 1988, *Biochem.* 252:47–54). Thus, properdin binding to C3b can be inhibited whether the C3b is unconjugated or conjugated to factor B to form C3bBb (alternative pathway C3 convertase). As shown in detail hereinafter in the Examples, anti-properdin antibodies can be screened and identified that block properdin binding to both C3b and C3bBb.

In accordance with a process of the present invention, properdin binding to C3b is inhibited by exposing properdin, in the presence of C3b, to an effective amount of an anti-properdin antibody, preferably a blocking antibody and most preferably a blocking antibody that lacks the ability to active the Fc$\gamma$ receptor upon binding to properdin, as described herein. Means for determining an effective amount of an antibody are well known in the art. The anti-properdin antibody can be a polyclonal or monoclonal antibody. The use of monoclonal antibodies is preferred. According to the invention, blocking antibodies against properdin have been identified and can be obtained from commercial sources (e.g., Quidel) or prepared using techniques well known in the art. Anti-properdin agents that are effective according to the invention, are preferably antibodies that selectively block alternative pathway activation, including blocking formation of complement activation products via the alternative pathway. However, in addition to such blocking antibodies, other blocking agents such as blocking peptides that are demonstrated to substantially or totally inhibit the alternative pathway-dependent formation of C3a, C5a and/or MAC after initiation of the alternative pathway or classical pathway or both are similarly contemplated by the invention as described herein.

Polyclonal antibodies against properdin can be prepared by immunizing an animal with properdin or an immunogenic portion thereof. Means for immunizing animals for the production of antibodies are well known in the art. By way of example, a mammal can be injected with an inoculum that includes properdin. Properdin can be included in an inoculum alone or conjugated to a carrier protein such as keyhole limpet hemocyanin (KLH). Properdin can be suspended, as is well known in the art, in an adjuvant to enhance its inmunogenicity. Sera containing immunologically active antibodies are then produced from the blood of such immunized animals using standard procedures well known in the art.

The identification of antibodies that immnunoreact specifically with properdin is made by exposing sera suspected of containing such antibodies to properdin to form a conjugate between antibodies and properdin. The existence of the conjugate is then determined using standard procedures well known in the art.

Properdin can also be used to prepare monoclonal antibodies against properdin and used as a screening assay to identify such monoclonal antibodies. Monoclonal antibodies are produced from hybridomas prepared in accordance with standard techniques such as that described by Kohler et al. (*Nature*, 256:495, 1975). Briefly, a suitable mammal (e.g., BALB/c mouse) is immunized by injection with properdin. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against properdin.

The inhibition of properdin binding to C3b is associated with inhibition of complement activation via the alternative pathway. As shown in detail hereinafter in the Examples, anti-properdin agents, preferably anti-properdin antibodies not only blocked properdin binding to C3b and C3bBb, but also blocked formation of products of the alternative pathway, including C5b-9, the Membrane-Attack Complex (MAC), which complex is the final end-product of complement activation. Still further, the data in the Examples show that antiproperdin agents, preferably anti-properdin antibodies, also block alternative pathway-dependent erythrocyte lysis mediated by MAC. Still further, the data in the Examples show that anti-properdin agents, preferably anti-properdin antibodies and their antigen-binding fragments such as F(ab)$_2$, are effective in inhibiting alternative pathway complement activation in models of cardiopulmonary bypass and in conditions of classical pathway complement activation.

The present findings are surprising and unexpected in view of the existing literature. For example, Schreiber et al. demonstrated that the alternative pathway could be functionally assembled by mixing all of the alternative pathway proteins except properdin; it was concluded that properdin is not required for alternative pathway initiation and amplification. (Schreiber, R. D., M. K. Pangbum, P. H. Lesavre and H. J. Muller-Eberhard, 1978, *Proc. Natl. Acad. Sci. USA* 75:3948–3952). Moreover, alternative pathway activation initiated by measles virus-infected HeLa cells in the absence of IgG was the same in the absence or presence of properdin. (Sissons, J. G., M. B. Oldstone and R. D. Schreiber, 1980, *Proc. Natl. Acad. Sci. USA* 77:559–562). These prior findings have led to the generally accepted hypothesis that "properdin is not an essential component for the activation of the pathway, but its presence does result in more rapid amplification of bound C3b" [emphasis added] (Pangburn, M. K. and H. J. Muller-Eberhard, 1984, Springer *Semin. Immunopathol.* 7:163–192). These references effectively teach away from the identification of properdin as a target for alternative pathway intervention. In contrast, according to the present invention, properdin is now identified as an essential component of and required for alternative complement pathway activation. Thus, a process of the present invention relates to the selective inhibition of alternative pathway by an antiproperdin agent. Such an agent surprisingly and effectively blocks the alternative complement cascade, including in conditions involving initiation of the classical complement pathway.

III. Process of Treating Pathological Injury

The ability to inhibit complement activation using a process of the present invention provides a therapeutic regimen for treatment of patients having clinical symptoms in which complement activation is deleterious. The complement system has been implicated as contributing to the pathogenesis of numerous acute and chronic disease states and conditions, as well as complications from a variety of medical procedures, including myocardial infarction (Moroko, P. R., C. B. Carpenter, M. Chiarello, M. C. Fishbein, P. Radva, J. D. Knostman, and S. L. Hale, 1978, Lab Invest. 48:43–47; Kilgore, K. S., G. S. Friedrichs, J. W. Homeister, and B. R. Lucchesi, 1994, Cardiovasc. Res. 28:437–44; Weisman, H. F., T. Bartow, M. K. Leppo, H. C. Marsh, G. R. Carson, M. F. Concino, M. P. Boyle, K. H. Roux, M. L. Weisfeldt; and D. T. Fearon, 1990, Science 249:146–151; Schafer, P. J., D. Mathey, F. Hugo, and S. Bhaki, 1986, *J. Immunol.* 137:1945–1949), stroke (Kaczorowski, S. L., J. K. Schiding, C. A. Toth and P. M. Kochanek, 1995, *J. Cereb. Blood Flow Metab.* 15:860–864; Morgan, B. P., P. Gasque, S. K. Singhrao, and S. J. Piddlesden, 1997, *Exp. Clin. Immunogenet.* 14: 19–23; Vasthare, U. S., R. H. Rosenwasser, F. C. Barone, and R. F. Tuma, 1993, FASEB J. 7:A424–429) ARDS (Mulligan, M. S., C. W. Smith, D. C. Anderson, R. F. Todd, M. Miyaska, T. Tamatani, T. B. Issekuts, and P. A. Ward, 1993, *J. Immunol.* 150:2401–2406; Solomkin, J. S., L. A. Cotta, P. S. Satoh, J. M. Hurst, and R. D. Nelson, 1985, *Surgery* 97:668–678; Mulligan, M. S., C. G. Yeh, A. R. Rudolph, and P. A.Ward, 1992, *J. Immunol.* 148:1479–1485; Anner, H., R. P. Kaufman, L Kobzik, C. R. Valeri, D. Shepro, and H. B. Hechtmnan, 1987, *Ann. Surgery* 206:642–648; Zilow, G., A. Sturm, U. Rother; and M. Kirschfink, 1990, *Clin. Exp. Immunol.* 79:151–157), reperfusion injury (Hsu, P., R. Simpson, T. F. Lindsay, T. Hebell, L. Kobzik, F. D. Moore, D. T. Fearon, and H. B. Hechtman, 1993, *Clin. Res.* 41:233 A; Lindsay, T. F., J. Hill, F. Ortiz, A. Rudolph, C. R. Valeri, H. B. Hechtman, and F. D. Moore, 1992, *Ann. Surg.* 216: 677–683; Rubin, B. B., A. Smith, S. Liauw, D. Isenman, A. D. Romaschin and P. M. Walker, 1990, *Am. J. Physiol.* 259:H525-H531; Hill, J., T. F. Lindsay, F. Ortiz, C G Yeh, H. B. Hechtman, and F. D. Moore, 1992, *J. Immunol* 149:1723–1729; Mulligan, M. S., E. Schmid, B. Beck-Schimmer, G. O. Till, H. P. Friedl, R. B. Brauer, T. E. Hugli, M. Miyasaka, R. L. Warner, K. J. Johnson, and P. A. Ward, 1996, *J. Clin. Invest.* 98:503–512; Pemberton, M., G. Anderson, V. Vetvicka, D. E. Justus, and G. D. Ross, 1993, *J. Immunol.* 150:5104–5113), sepsis/septic shock (Hack, C. E., J. H. Nuijens, R. J. F. Felt-Bersma, W. O. Schreuder, A. J. M. Eerenberg-Belmer, J. Paardekooper, W. Bronsveld, and L. G. Thijs, 1989, *Am J Med* 86:20–26; Bengston, A., and M. Heideman, 1988, *Arch. Surg.* 23:645:649; Stevens, J, H., P. O'Hanley, J. M. Shapiro, F. G. Mihn, P. S. Satoh, J. A. Collins and T. A. Raffin, 1986, *J. Clin. Invest.* 77:1812–1816; Wakabayashi, G., J. A. Gelfand, W. K. Jung, R. J. Connolly, J. F. Burke, and C. A. Dinarello, 1991, *J. Clin. Invest.* 87:1925–1935), thermal burns (Solomkin, J. S., R. D. Nelson, D. E. Chenoweth, L. D. Solem and R. L. Simmons, 1984, *Ann. Surg.* 200, 742–746; Bjornson, A. B., S. Bjornson and W. A. Altemeier, 1981, *Ann. Surg.* 194:224–231; Gelfand, J. A., M. Donelan, and J. F. Burke, 1983, *Ann. Surg.* 198:58–62; Gelfand, J. A., M. Donelan, and J. F. Burke, 1982, *J. Clin. Invest.* 70:1170–1176), post-cardiopulmonary bypass inflammation (Salama, A., F. Hugo, D. Heinrich, R. Hoge, R. Miller, V. Keifel, C. Muller-Eckhardt, and S. Bakdi, 1988, *N.Engl. J. Med.* 318:408–414; Chenoweth, D. E., S. W. Cooper, T. E. Hugli, R. W. Stewart, E. H. Blackstone and J. W. Kirklin, 1981, *N.Engl. J. Med.* 304:497–503; Moore, F. D., K. G. Warner, S. Assoussa, C. R. Valeri, and S. F. Khuri, 1987, *Ann. Surg.* 208:95–103; Rinder, C. S., H. M. Rinder, B. R. Smith, J. C. K. Fitch, M. J. Smith, J. B. Tracey, L. A. Matis, S.P. Squinto, and S. A. Rollins, 1995, *J. Clin Invest.*96:1564–1572), hemodialysis (Hakim, R. M., J. Breillatt, J. M. Lazarus, and F. K. Port, 1984, *New Eng. J. Med.* 311:878–882), use of radiographic contrast media (Arroyaue, C. M., and E. M. Tan, 1977, *Clin. Exp. Immunol.* 29:89–94), transplant rejection (Pruitt, S. K., W. M. Baldwin, H. C. Marsh, S. Lin, C. G. Yeh, and R. R. Bollinger, 1991, *Transplantation* 52:868–873; Leventhal, J. R., A. P. Dalmasso, J. W. Cromwell, J. L. Platt, C. J. Bolman, and A. J. Matas, 1993, *Transplantation* 55:857–865; Dalmasso, A. P., G.M. Vercelloti, R. J. Fischel, R. J. Bolman, F. H. Bach and J. L. Platt, 1992, *Am. J. Pathol.* 140:1157–1166; Xia, W., D. T. Fearon, F. D. Moore, F. J. Schoen, F. Ortiz and R. L. Kirkman,1992, *Transplant Proc.* 24:479–480), rheumatoid arthritis (Mollnes, T. E., T. Lea, O. J. Mellbye, J. Pahle, 0. Grand, and M. Harboe, 1986, *Arth. Rheum.* 29:715–721; Morgan, B. P., R. H. Daniels, and B. D. Williams, 1988, *Clin. Exp. Immunol.* 73:473–478), multiple sclerosis (Linington, C., B. P. Morgan, N. J. Scolding, S. Piddlesden, and P. Wilkins, 1989, *Brain.* 112:895–911; Sanders, M. E., C. L. Koski, D. Robbins, M. L. Shin, M. M. Frank, and K. A. Joiner, 1986, *J. Immunol.* 135:4456), myasthenia gravis (Biesecker, G. and C. M. Gomez, 1989, *J. Immunol.* 142:2654–9; Nakano, S., and A. G. Engel. 1993 *Neurology* 43:1167–72), pancreatitis (Roxvall, L., A. Bengtson, and M. Heideman, 1989, *J. Surg. Res.* 47:138–143; Roxvall, L., A. Bentston, and M. Heidman, 1990 *Arch. Surg.* 125:918–921) and Alzheimer's disease (Eikelenboom, P., C. E. Hack, J. M. Rozemuller, and F. C. Stam, 1989, *Virchows Arch.* (Cell pathol.) 56:259–62; Rogers, J. N. R. Cooper, and S. Webster, 1992, *Proc. Natl. Acad. Sci. USA* 89:10016–20). While complement may not be the only cause of the pathogenesis in these conditions, it is nevertheless a major pathological mechanism and represents an effective point for clinical control in many of these disease states.

Complement activation products have been detected in biological fluids or diseased tissues isolated from patients with many of the aforementioned conditions, and a correlation between the severity of the clinical indication with the abundance of complement activation products has been demonstrated for some diseases (Zilow, G., A. Sturm, U. Rother, and M. Kirschfink, 1990, *Clin. Exp. Immunol.* 79:151–157; Hack, C. E., J, H. Nuijens, R. J. F. Felt-Bersma, W. O. Schreuder, A. J. M. Eerenberg-Belmer, J. Paardekooper, W. Bronsveld, and L. G. Thijs, 1989, *Am. J. Med.* 86:20–26; Gelfand, J. A., M. Donelan, and J. F. Burke, 1983, *Ann. Surg.* 198:58–62). The most compelling evidence directly implicating complement in the pathogenesis of a diverse group of human diseases comes from studies using art accepted animal models of such diseases. In such animal models, removal of classical pathway-activating antibodies (Fischel, R. J., R. M. Bolman, J. L. Platt, K. S. Naharian, F. H. Bach, and J. J. Matas, 1990, *Trans. Proc.* 22:1077–1083; Platt, J. L., R. J. Fischel, A. J. Matas, S. A. Reif, R. M. Bolman., and F. H. Bach, 1991, *Transplantation* 52:214–230), depletion of complement by cobra venom factor (Moroko, P. R., C. B. Carpenter, M. Chiarello, M. C. Fishbein, P. Radva, J. D. Knostman, and S. L. Hale, 1978, *Lab. Invest.* 48:43–47; Mulligan, M. S., C. W. Smith, D. C. Anderson, R. F. Todd, M. Miyaska, T. Tamatani, T. B. Issekuts, and P. A. Ward, 1993, *J. Immunol.* 150:2401–2406; Gelfand, J. A., M. Donelan, and J. F. Burke, 1983, *Ann. Surg.* 198:58–62; Leventahal, J. R., A. P. Dalmasso, J. W. Cromwell, J. L. Platt, C. J. Bolman, and A. J. Matas, 1993, *Transplantation* 55:857–865), inhibition of complement activity (Weisman, H. F., T. Bartow, M. K. Leppo, H. C. Marsh, G. R. Carson, M. F. Concino, M. P. Boyle, K. H. Roux, M. L. Weisfeldt, and D. T. Fearon, 1990, *Science* 249:146–151; Mulligan, M. S., C. G. Yeh, A. R. Rudolph, and P. A. Ward, 1992, *J. Immunol.* 148:1479–1485; Pemberton, M., G. Anderson, V. Vetvicka, D. E. Justus, and G. D. Ross, 1993, *J. Immunol.* 150:5104–5113), or testing in animals genetically deficient in specific complement components (Gelfand, J. A., M. Donelan, and J. F. Burke, 1983, Ann. Surg. 198:58–62; Watson, W. C., and A. C. Townes, 1985, *J. Exp. Med.* 162:1878–1883), have all been shown to abrogate or delay pathogenesis.

Inherited deficiencies have been recognized in humans for nearly every complement component (Liszewski, M. K. and J. P. Atkinson, 1993, *Fundamental Immunology*, Third Edition. Edited by W. E. Paul. Raven Press, Ltd. New York). Deficiencies of components of the same pathway cause similar clinical problems. Classical pathway component deficiencies (C1, C4, C2) commonly cause infections by a variety of pyrogenic organisms and immune complex diseases, as does deficiency of C3. Alternative pathway component deficiencies (P, D) often results in Neisserial infections. There is no evidence that properdin deficiency causes increased susceptibility to immune complex disease or to infections with organisms other than Neisseria. No homozygous deficiencies in Factor B have been described (Morgan, B. P. and M. J. Walport, 1991, *Immunology Today* 12:301–306).

Inactivation of the alternative complement pathway is particularly useful in subjects where activation is associated with the pathological effects of disease states. As set forth hereinbefore, complement activation is known to be associated with a large and diverse group of disease states. Complement activation via the alternative pathway is particularly prominent in states of acute injury.

The complement-induced fulminant meningococcal septicemia in patients with systemic meningococcal disease is likely caused predominantly by activation of the alternative pathway (Brandtzaeg et al., *Journal of Infectious Disease*, 173:647–55, 1996). In patients with adult respiratory distress syndrome (ARDS), complement activation occurred only via the alternative pathway for the first 48 hours (Zilow et al., *J. Exp. Immunology*, 79: 151–57, 1990). An agent that suppresses complement activation via both pathways has been used to treat post-ischemic myocardial inflammation and necrosis in animal models of cardiovascular disease (Weisman et al., *Science*, 249:146–71, 1990). According to Weisman et al., the acute tissue injury associated with numerous autoimmune diseases is the result of complement activation. Complement induced tissue injury is found in immune complex-induced vasculitis, glomerulonephritis, hemolytic anemia, myasthenia gravis, type II collagen-induced arthritis, and ischemia.

The role of the alternative complement pathway in inducing ischemic cardiac damage during reperfusion has also been reported (Amsterdam et al., Amer. J. Physiol., 268: H448-H457, 1995). Mulligan et al. 1992, *J. Immunol.* 148:1479–1485 reported that complement activation plays a role in a variety of tissue injuries including glycogen-induced peritonitis, lung and dermal injury after intra-alveolar or intra-dermal deposition of IgG immune complexes, acute lung injury resulting from intravascular activation of complement after injection of cobra venom factor, and acute skin and lung injury after thermal trauma.

A variety of medical procedures utilize extracorporeal circulation (ECC), including hemodialysis, plasmapheresis, plateletpheresis, leukopheresis, extracorporeal membrane oxygenation (ECMO), heparin-induced extracorporeal LDL precipitation (HELP) and most commonly cardiopulmonary bypass (CPB). These procedures expose blood or blood products to foreign surfaces that may alter normal cellular function and hemostasis. For example, it is well-established that CPB often leads to complex inflammatory responses that result in post-surgical complications, generally termed "post-perfusion syndrome". Among these postoperative events are respiratory failure, bleeding disorders, renal dysfunction and, in the most severe cases, multiple organ failure (Wan, S., J-L.LeClerc, and J-L. Vincent, 1997, *Chest* 112:676–692). The primary suspected cause of these CPB-related problems is inappropriate activation of complement during the bypass procedure (Chenoweth, K., S. Cooper, T. Hugli, R. Stewart, E. Blackstone, and J. Kirklin, 1981, *N. Engl. J. Med.* 304:497–503; P. Haslam, P. Townsend, and M. Branthwaite, 1980, *Anaesthesia* 25:22–26; J. K. Kirklin, S. Westaby, E. Blackstone, J. W. Kirklin, K. Chenoweth, and A. Pacifico, 1983, *J. Thorac. Cardiovasc. Surg.* 86:845–857; Moore, F. D., K. G. Warner, B. A. Assousa, C. R. Valeri, and S. F. Khuri, 1988, *Ann. Surg.* 208:95–103; J. Steinberg, D. Kapelanski, J. Olson, and J. Weiler, 1993, *J. Thorac. Cardiovasc. Surg.* 106:1901–1918). While it appears that blood contact with the tubing and oxygenator surfaces of the CPB circuit results in activation of the alternative complement pathway (Chenoweth, K., S. Cooper, T. Hugli, R. Stewart, E. Blackstone, and J. Kirklin, 1981, *N. Engl. J. Med.* 304:497–503; Velthuis, H., P. G. M. Jansen, C. E. Hack, L. Eijsan, and C. R. H. Wildevuur, 1996, *Ann. Thorac. Surg.* 61:1153–1157), there is also evidence that the classical complement pathway is activated during CPB (Wachtfogel, Y. T., P. C. Harpel, L. H. Edmunds, Jr. and R. W. Colman, 1989, *Blood* 73:468–471). Moreover, the classical complement cascade is initiated after the termination of CPB due to the addition of protamine to a patient's blood. Protamine is utilized clinically to bind and remove the heparin that is added as an anti-coagulant during surgery. The heparin-protamine complexes cause significant activation of the classical complement pathway (Steinberg, J., D. Kapelanski, J. Olson, and J. Weiler, 1993 *J. Thorac. Cardiovasc. Surg.* 106:1901–1918), further contributing to post-perfusion syndrome.

Activated complement species, particularly the anaphylotoxins C3a and C5a, are known to elicit a variety of inflammatory responses from many cell types. For example, C5a can up-regulate cell adhesion molecule expression on neutrophils, and can also invoke lysosomal enzyme and free radical release from both neutrophils and monocytes (Chenoweth, D. and T. Hugli, 1978, *Proc. Natl. Acad. Sci. USA* 75:3943–3947; Fletcher, M. P., G. Stakl, and J. Longhurst, 1993, *Am. J. Physiol.* 265:H1750-H1761). Likewise, C5a can activate platelets, rendering them incapable of normal clotting function (Foreman, K. E., A. A. Vaporciyan, B. K. Bonish, M. L. Jones, K. J. Johnson, M. M. Glovsky, S. M. Eddy, and P. A. Ward, 1994, *J. Clin. Invest.* 94:1147–1155). Finally, the terminal activated complement product, C5b-9 (membrane-attack complex), can also affect platelet and endothelial cell function (Foreman, K. E., A. A. Vaporciyan, B. K. Bonish, M. L. Jones, K. L. Johnson, M. M. Glovsky, S. M. Eddy, and P. A. Ward, 1994, *J. Clin. Invest.* 94:1147–1155; Hattori, R., K. K. Hamilton, R. D. Fugate, R. P. McEver, and P. J. Sims, 1989, *J. Biol. Chem.* 264:9053–9060). It is the actions of these complement species on neutrophils, platelets and other circulatory cells that likely lead to the various problems that arise after CPB.

Recently, there has been direct experimental evidence that complement activation is, in fact, responsible for many of the changes involving dysfunction of the immune and hemostatic systems seen after CPB. Using soluble complement receptor type 1 (sCR1), which prevents activation of both the classical and alternative complement pathways, Gillinov, A. M., P. A. DeValeria, J. A. Winkelstein, I. Wilson, W. E. Curtis, D. Shaw, C. G. Yeh, A. R. Rudolph, W. A. Baumgartner, A. Herskowitz, and D. E. Cameron, (1993, *Ann. Thorac. Surg.* 55:619–624) demonstrated that inhibiting complement activation improved pulmonary vascular resistance in pigs undergoing a CPB procedure. Utilizing an ex vivo model of simulated CPB, Rinder et al. (1995, supra) showed that addition of a monoclonal antibody to C5 significantly reduced the neutrophil and platelet activation that occurred during the bypass procedure. The C5 antibody blocks the cleavage of C5 in both the classical and alternative complement pathways, and thus prevents the production of both the membrane-attack complex and the anaphylotoxin, C5a. The use of such an anti-C5 monoclonal antibody for reducing complement, platelet or leukocyte activation or platelet—leukocyte adhesion resulting from passage of a patient's blood via extracorporeal circulation is described in WO95/25540 [PCT/US95/03614].

IV. Pharmaceutical Compositions

A process of the present invention can thus be used to inhibit complement activation via the alternative pathway, including to inhibit the formation of complement activation products via the alternative pathway, in patients by administering to a patient in need of complement inactivation an effective inhibiting amount of an anti-properdin agent, preferably an anti-properdin antibody or antigen-binding domain thereof. Preferably, the anti-properdin agent, most preferably an anti-properdin antibody or antigen-binding domain thereof, is administered in the form of a pharmaceutical composition.

Such a pharmaceutical composition comprises a therapeutically effective amount of an anti-properdin agent, preferably an anti-properdin antibody formulated together with one or more non-toxic pharmaceutically acceptable carriers are disclosed. As used herein, the term "pharmaceutically acceptable carrier" means a non-toxic, insert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to humans and other animals orally, rectally, parenterally, intracisternally, intravaginally, intraperitoneally, transdermally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral composition can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in preparation of injectables.

The injectables formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which in turn, may depend upon crystal size and crystalline form. Alternatively, delayed absorption of a parenterally administered drug is accomplished by dissolving or suspending the drug in an oil vehicle. Injection depot forms are made by forming micorencapsule matrices of the drug in biodegradable polymers such as polylactide-polylactide-polyglycolide. Depending upon the ratio of drug to polymer and the nature of the particular polymer employed, the rate of drug release can be controlled. Examples of other biodegradable polymers include poly (orthoesters) and poly (anhydrides) Depot injectable formulations are also prepared by entrapping the drug in liposomes of microemulsions which are compatible with body tissues.

Compositions for rectal or vaginal administration are preferably suppositories which can be prepared by mixing the compounds of this invention with suitable non-irritating excipients or carries such as cocoa butter, polyethylene glycol or a suppository wax which are solid at ambient temperature but liquid at body temperature and therefore melt in the rectum or vaginal cavity and release the active compound.

Solid compositions of a similar type may be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings well known in the pharmaceutical formulating art. In such solid dosage forms the active compound may be admixed with at least one inert diluent such as sucrose, lactose or starch. Such dosage forms may also comprise, as is normal practice, additional substances other inert diluents, e.g., tableting lubricants and other tableting acids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicaters and polyamide powder, or mixtures of these substances. Sprays can additionally contain customary propellants such as chlorofluorohydrocarbons.

Figure 4:
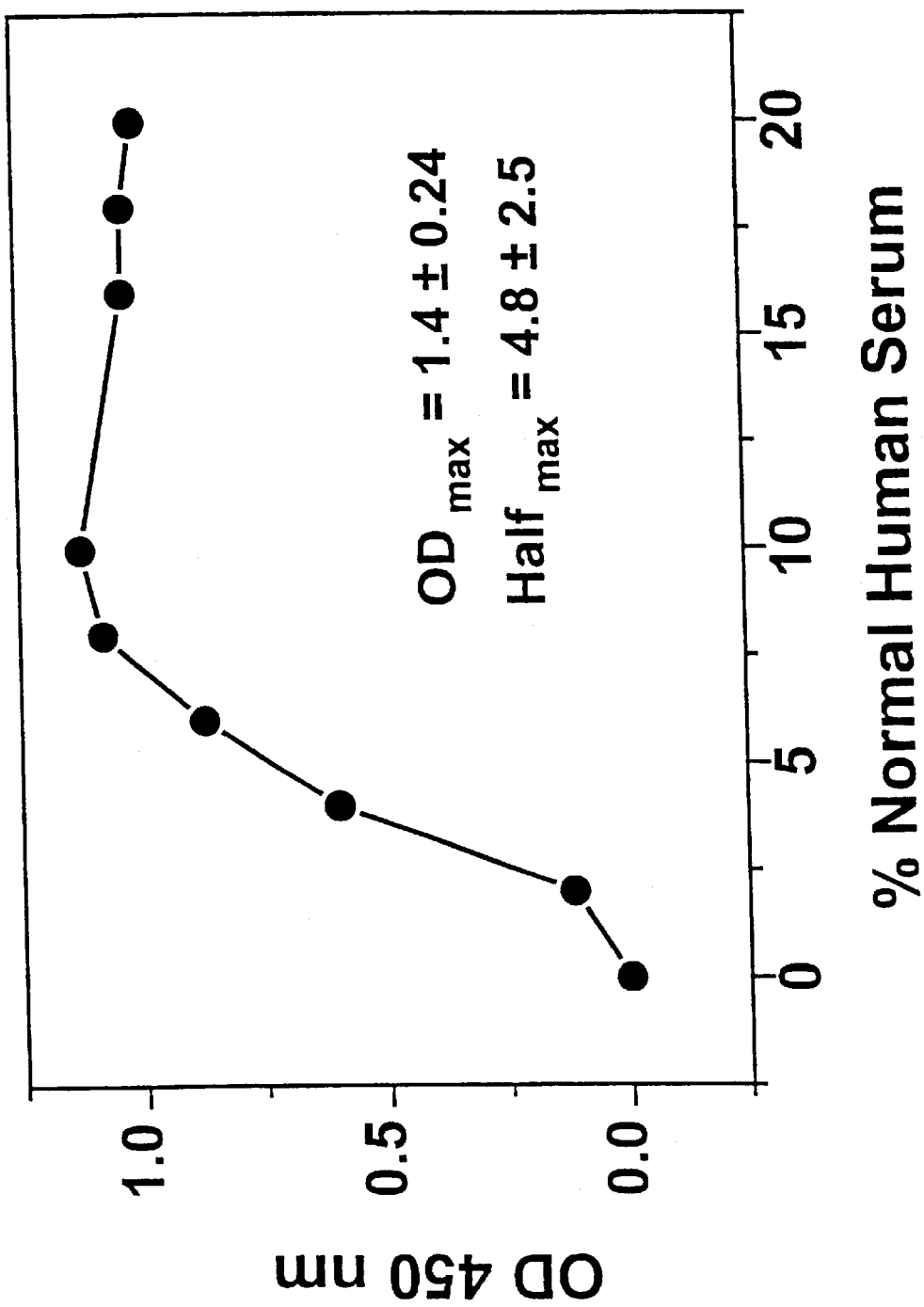
FIG. 4 shows the effects of human serum containing complement components on the deposition of the membrane attack complex (MAC).
Figure 5:
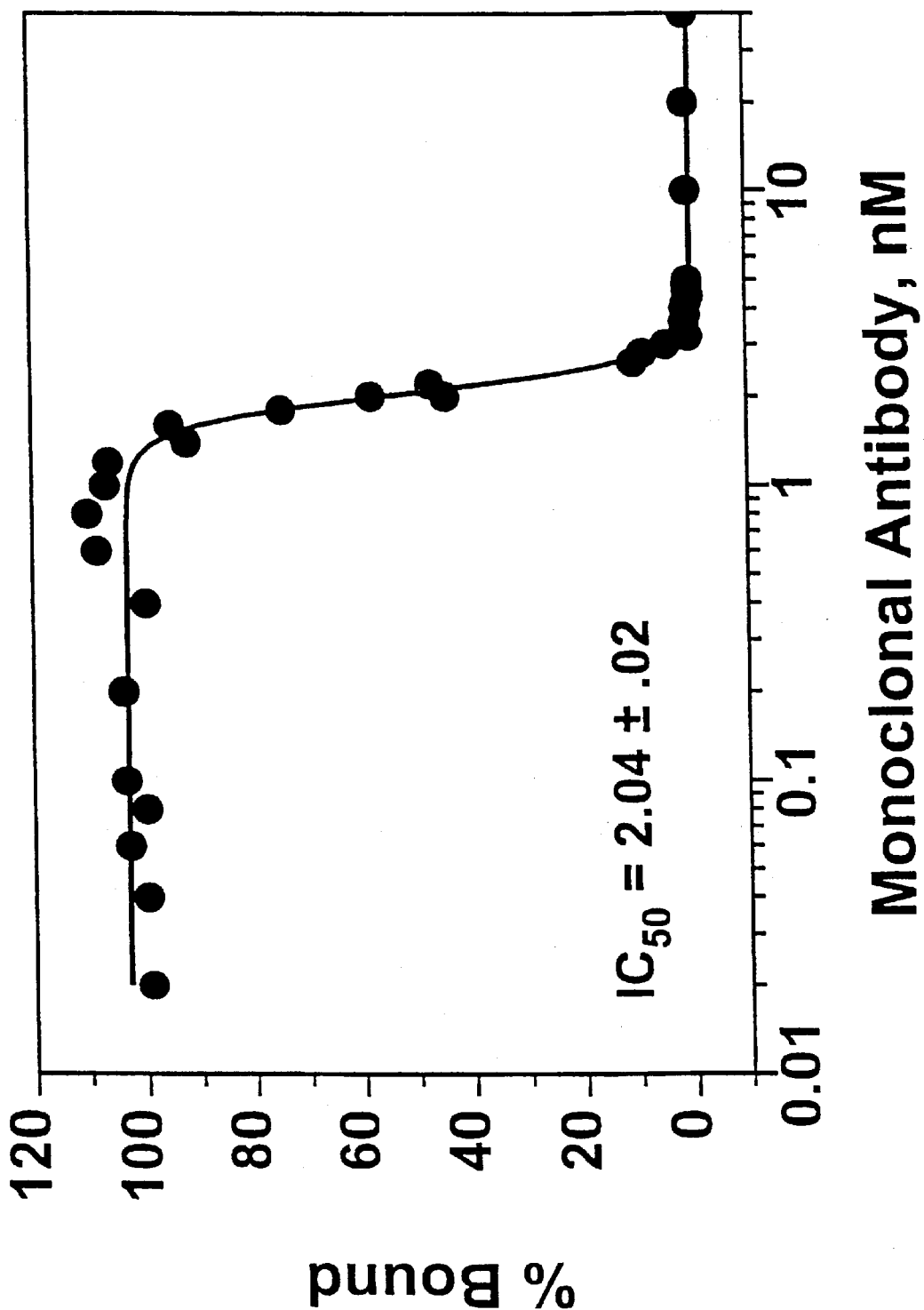
FIG. 5 shows the inhibition of membrane attack complex (MAC) deposition caused by an anti-properdin monoclonal antibody.

Transdermal patches have the added advantages of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The Examples that follow illustrate preferred embodiments of the present invention and are not limiting of the specification and claims in any way.

EXAMPLE 1

C3b-Properdin Binding

Polystyrene microtiter plates were coated with human C3b (0.5 μg/50 μl per well) (Calbiochem, San Diego, Calif., Cat. No. 204860) in Veronal buffered saline (VBS): (5 mM diethyl barbiturate, 120 mM NaCl, 5 mM $MgCl_2$, 5 mM EGTA) overnight at 4° C. After aspirating the C3b solution, wells were blocked with VBS containing 0.5% human serum albumin (HSA) (Sigma Chemical Company, St. Louis, Mo., Cat. No. A9511) for 2 hours at room temperature. Wells without C3b coating served as background controls. Aliquots of human properdin (or factor P) (Advanced Research Technology, San Diego, Calif., Cat. No. A139) at varying concentrations in blocking solution were added to the wells. Following a 2 hour incubation at room temperature, the wells were extensively rinsed with VBS.

C3b-bound properdin was detected by the addition of mouse monoclonal anti-human properdin antibody (detection antibody) (Quidel, San Diego, CA, anti-human properdin monoclonal antibody P#2, Cat. No. A235) at 1:1000 dilution in blocking solution, which was allowed to incubate for 1 hour at room temperature. After washing the plates with VBS, a peroxidase-conjugated goat anti-mouse antibody (1:1000 dilution in blocking solution) (Sigma Chemical Company) was added and allowed to incubate for 1 hour. The plate was again rinsed thoroughly with VBS, and 100 μl of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 μl of phosphoric acid, and the plate was read at 450 nm in a microplate reader (e.g., SPECTRA MAX 250, Molecular Devices, Sunnyvale, Calif.). The estimated $K_d$ of properdin binding to C3b was based on the concentration of properdin at 50% maximal binding (Microcal Origin Program).

The ability of a murine anti-human properdin monoclonal antibody (blocking antibody) to inhibit C3b-P binding was evaluated by adding varying concentrations of this antibody (blocking antibody, Quidel, anti-human properdin monoclonal antibody P#1, Cat. No. A233) to a constant concentration of properdin (2 nM). The amount of properdin bound to C3b was detected with the antibody detection system described above.

As shown in FIG. 1, human properdin binds to C3b, which has been immobilized onto microtiter plate wells. The apparent binding constant from these data, defined as the concentration of properdin needed to reach half-maximal binding, is approximately 1 nM. When blocking anti-properdin monoclonal antibody is added along with properdin in this assay, dose-dependent inhibition of properdin binding to C3b is observed (FIG. 2). The $IC_{50}$ value of 1 nM indicates that the antibody binds with high-affinity to properdin, thereby blocking its interaction with C3b.

EXAMPLE 2

C3b(Bb)-Properdin Binding

This assay was carried out as described in Example 1 above with some changes. Briefly, microtiter wells were coated with C3b, washed, blocked and incubated with various concentrations of normal human serum (NHS) (Sigma Chemical Company, Cat. No. S1764) diluted in blocking solution for 2 hours at room temperature. Under the conditions of this binding assay, factor B in serum will bind solid phase-bound C3b and, after cleavage by factor D in serum, generates C3bBb. Properdin is known to bind C3bBb with high affinity (Farries, T. C., P. J. Lachmann, and R. A. Harrison, 1988, Biochem. 252:47–54). Uncoated wells served as background controls. After washing, bound-properdin was detected with the anti-properdin antibody as described in Example 1 above.

To evaluate the effect of the blocking antibody to inhibit properdin binding to C3b(Bb), various concentrations of the blocking antibody described in Example 1 above were added to a fixed concentrations of serum (4% in blocking solution). The amount of properdin bound to C3b(Bb) was detected using the detection system described in Example 1 above.

In addition to purified properdin, properdin in serum can bind to immobilized C3b. Since serum also contains factor B, which binds C3b with a resulting conversion to Bb after cleavage by factor D, it is likely that serum-derived properdin is binding the C3bBb complex in this assay format. When the blocking anti-properdin monoclonal antibody of Example 1 is added with human serum to C3b-coated wells, there is a dose-dependent inhibition of properdin binding to C3bBb (FIG. 3). Again, the $IC_{50}$ value in this assay is 1–2 nM, consistent with the results obtained in FIG. 2 described in Example 1 above.

EXAMPLE 3

Alternative Pathway-Dependent MAC Assay

The binding data of Examples 1 and 2above reveal that the properdin monoclonal antibody prevents the binding of properdin to C3b and the functional C3 convertase (C3bBb). Since the literature suggests that properdin stabilizes the C3 convertase, it was of interest to us to determine whether the properdin antibody might appreciably affect the terminal aspects of the alternative complement cascade. The final end product of this pathway is the C5b-9 membrane-attack complex (MAC). To analyze the effects of the properdin antibody on MAC formation via the alternative pathway, an assay was utilized in which bacterial LPS was used as a substrate to initiate the alternative complement pathway cascade.

Previous studies have demonstrated that lipopolysaccharide (LPS) from *Salmonella typhosa* (*S. Typhosa*) (Sigma Chemical Company, Cat. No. 6386) serves as a potent substrate for complement alternative pathway activation (Clardy, C. W., 1994, *Infect. Immun.* 62:4539–4555). Microtiter wells were coated with LPS (2 μg/50 μl per well) in VBS overnight at 4° C. Uncoated wells served as background controls. After aspirating the LPS solution, wells were treated with blocking solution and incubated with various concentrations of normal human serum. Following a 3 hour incubation at 37° C., deposited MAC was detected with mouse anti-human soluble C5b-9 monoclonal antibody (Quidel, Cat. No. A239) using standard ELISA methodologies essentially as described in the Examples above. The effect of the blocking antibody on the MAC formation was evaluated by adding various concentrations of blocking antibody to a fixed concentration of serum (4% in blocking solution). The amount of inhibition of soluble C5b-9 formation was determined using the antibody detection system described in the Examples above.

As demonstrated in FIG. 4, addition of increasing amounts of normal human serum, which contains all of the complement components, resulted in increased MAC deposition on the LPS surface. The formation of MAC in this assay could be completely prevented by the addition of the properdin monoclonal antibody, as seen in FIG. 5. These data indicate that properdin does not merely stabilize and alter the kinetics of the alternative pathway, as suggested in the literature, but demonstrates for the first time that properdin is in fact necessary for progression of the cascade.

EXAMPLE 4

Alternative Pathway—Dependent Hemolysis

To confirm and extend these results, the properdin antibody was examined in another assay of the alternative pathway. Rabbit erythrocytes initiate the alternative complement cascade, and the resulting formation of MAC causes lysis of these cells. If the properdin antibody is capable of complete inhibition of the alternative pathway, then addition of the reagent to rabbit erythrocytes bathed in human serum should prevent cellular lysis. This can be assayed by examining the light scattering caused by intact red blood cells; lysed cells do not diffract light, and there is a consequent reduction in scattered light. It is well established that rabbit erythrocytes specifically activate the complement alternative pathway, with a resulting lysis of the cells by the C5b-9 complex (Nolan, K. F. and K. B. M. Reid, 1993, Properdin. *Methods Enzymol*. 223:35–47). Normal human serum, at various concentrations in Gelatin Veronal Buffer (GVB) (Advanced Research Technology) with 5 mM $MgCl_2$ and 10 mM EGTA, was incubated with 37° C. with a fixed number of rabbit erythrocytes (Advanced Research Technology). A progressive decrease in light scatter (due to lysis of intact cells) was measured at 595 nm as a function of time in a temperature-controlled ELISA plate reader (Polhill et al., *J. Immunol*. 121:383:370). To determine the ability of blocking antibody to inhibit hemolysis of rabbit erythrocytes, various concentrations of the blocking antibody were added to a fixed concentration of normal human serum (8%) and the assay was performed as described above. The data were recorded and analyzed with a SpectraMax plate reader and software.

Figure 6:
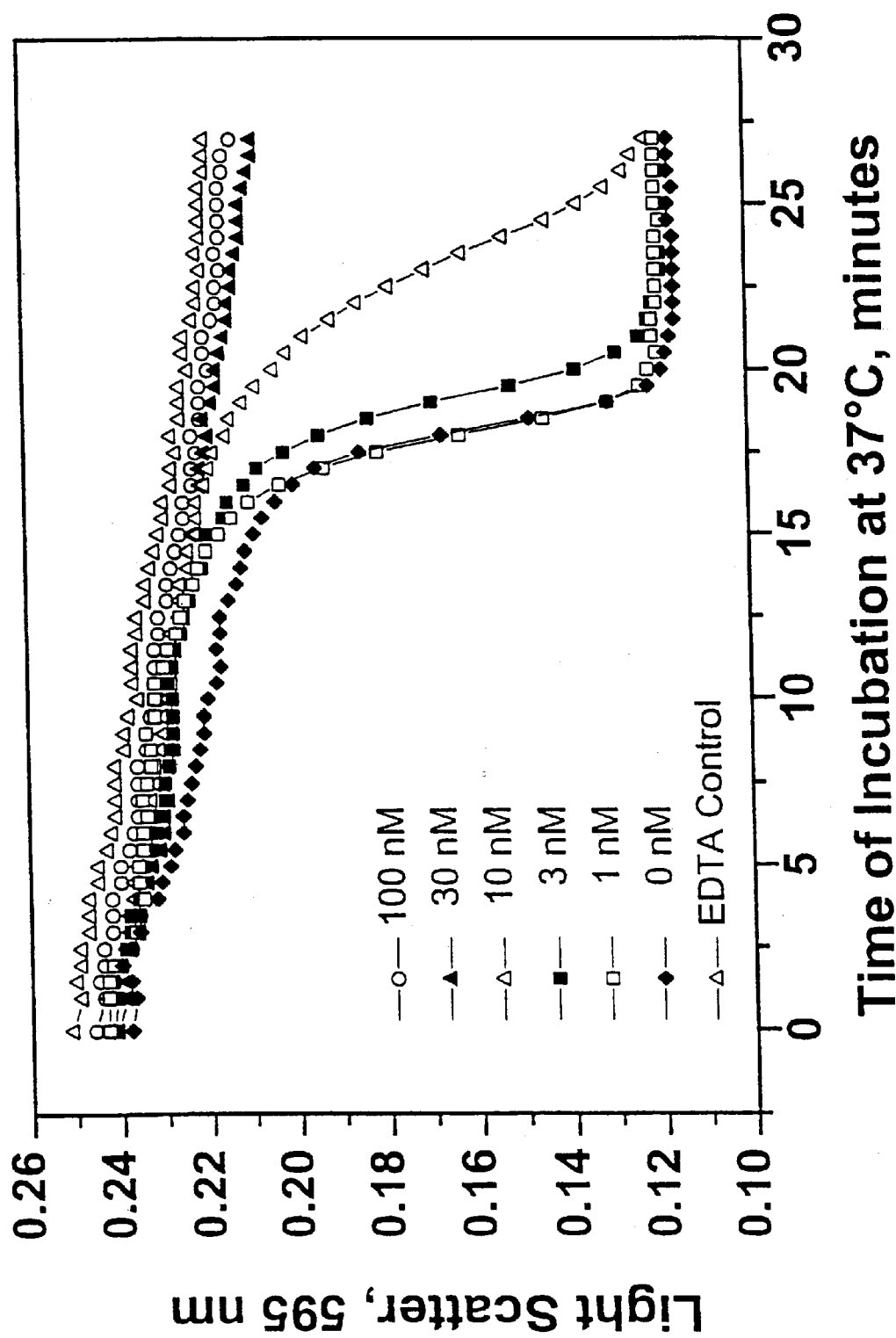
FIG. 6 shows the effects on an anti-properdin monoclonal antibody on rabbit erythrocyte lysis.

As shown in FIG. 6, addition of serum in the absence of properdin antibody resulted in lysis of the cells and a dramatic reduction in light scattering. Addition of increasing concentrations of the antibody caused a decrement in erythrocyte lysis, with 30 nM antibody completely blocking MAC-mediated cellular destruction. These results confirm that monoclonal antibodies that bind and block properdin interaction with C3 convertase are potent reagents that can completely abrogate the effects of the alternative complement pathway.

Skilled artisans recognize and accept that in vitro studies of complement are representative of and predictive of the in vivo state of the complement system. By way of example, the use of in vitro ELISA (enzyme-linked immunosorbent assay) procedures to detect properdin associated with lipopolysaccharide (LPS) is a "simple, rapid and reliable method for the assessment of complement function particularly the detection of complement deficiency states" (Fredrikson et al., *J. Immunol. Meth*., 166:263–70, 1993). The authors conclude that the in vitro technique can be used in vivo with the same likelihood of success in detecting alternative complement pathway activation in disease states. Similarly, the use of a 34-amino acid peptide to study properdin binding with C3b using an in vitro hemolysis test was found to be an appropriate indication of both the role of properdin during infection and the mechanism of C3 convertase stabilization (Daoudaki et al., *J. of Immun*., 140:1577–80, 1988).

Still further, the standard rabbit erythrocyte hemolysis assay (described in detail herein in Example 4), which assay is used to measure alternative complement pathway activity, is accepted in the art as being the "most convenient assay for the activity of the human alternative pathway" (Pangburn, *Meth. In Enzymology*, 162:639–53, 1988).

EXAMPLE 5

Cardiopulmonary Bypass: Tubing Loop Model

To test the effect of a blocking anti-properdin monoclonal antibody, as described in Examples 1–4 above, on inhibition of complement activation in cardiopulmonary bypass (CPB), a tubing loop model of CPB as described by Gong, J., R. Larsson, K. N. Edkahl, T. E. Mollnes, U. Nilsson, and B. Nilsson, 1996, *J. Clin. Immunol*. 16:222–229 was utilized. Whole blood from a healthy donor was collected into a 7-ml vacutainer tube (Becton Dickinson, San Jose, Calif.) containing 20 U of heparin/mnl of blood. Polyethylene tubing like that used during CPB (PE 330; I.D., 2.92 mm; O.D., 3.73 mm; Clay Adams, NJ) was filled with 0.5 ml of the heparinized human blood and closed into a loop with a short piece of silicon tubing. Heparinized blood containing 20 mM EDTA (which inactivates complement) served as a background control. Sample and control tubing loops were rotated vertically in a water bath for 1 hour at 37° C. After incubation, blood samples were transferred into 1.7 ml siliconized eppendorf tubes which contained 0.5 M EDTA to give a final EDTA concentration of 20 mM. The samples were centrifuged (4000×g for 5 minutes at 4° C.) and the plasma was collected. The plasma samples were diluted to 10% with sample diluent buffer and the amounts of C3a as well as soluble MAC (sMAC) were determined using ELISA assay kits following the manufacturer's instructions (Quidel, Catalog Nos. A015 for C3a and A009 for C5b-9/MAC). For complement inhibition studies, various concentrations (100–600 nM) of the blocking anti-properdin monoclonal antibody described in Examples 1–4 were added to the heparinized blood immediately before circulation for 1 hour at 37° C. After circulation/rotation in a 37° C. water bath for 1 hour, aliquots were analyzed for soluble MAC and C3a as described above using ELISA assay kits (Quidel).

Using this simplified CPB paradigm in which standard CPB tubing was partially filled with fresh human blood, leaving an air-blood interface and where the tubing is joined end-to-end with a silicon sleeve to form a loop, such that this blood-filled loop is rotated in a heated water bath (37°) to simulate the movement of blood through a bypass circuit, there is marked activation of complement during the rotation of the blood in the tubing. Importantly, the blocking anti-human properdin antibody causes significant inhibition of this complement activation. This can be seen in FIG. 7, where the formation of soluble membrane-attack complex (sMAC) in the loop model is nearly completely inhibited by 100 nM anti-properdin antibody. Likewise, the same amount of antibody causes a significant reduction in C3a formation (FIG. 7).

This is the first demonstration of the effectiveness of an agent that selectively inhibits alternative pathway activation in a model of CPB. In contrast, all prior agents to date that have been used experimentally to inhibit complement activation in CPB protocols inhibit both the classical and alternative complement pathways (e.g., Gillinov, A.M., P. A. DeValeria, J. A. Winkelstein, I. Wilson, W. E. Curtis, D. Shaw, C. G. Yeh, A. R. Rudolph, W. A. Baumgartner, A. Herskowitz, and D. E. Cameron, 1993, *Ann. Thorac. Surg.* 55:619–624; Rinder, C. S., H. M. Rinder, B. R. Smith, J. C. K. Fitch, M. J. Smith, J. B. Tracey, L. A. Matis, S.P. Squinto, and S. A. Rollins, 1995, *J. Clin. Invest.* 96:1564–1572). Because it has been suggested that both the classical and alternative pathways are activated during CPB (Wachtfogel, Y. T., P. C. Harpel, L. H. Edmunds, Jr. and R. W. Colman, R. W., 1989, *Blood* 73:468–471), these results with an alternative pathway targeting agent are particularly surprising.

EXAMPLE 6

Blocking Agents: Lack of Fcγ Receptor Activation

As described in Example 5above, the blocking anti-properdin monoclonal antibody potently inhibits soluble MAC and C3a generation in a tubing loop model of cardiopulmonary bypass. The proinflammatory agents (C5a, C3a and sMAC) generated by complement activation are known to activate leukocytes, platelets and endothelial cells. As a marker for neutrophil activation, serum levels of neutrophil elastase in whole blood in the tubing loop model were also determined. As expected, elastase levels in blood samples incubated in the tubing loop were increased over levels in control samples. However, release of elastase was not inhibited by the anti-properdin monoclonal antibody. Rather, there was an unexpected increase in serum elastase levels with increasing antibody concentrations. If inumune-complexes are generated when the antiproperdin monoclonal antibody is added to blood containing properdin, these immune-complexes could interact with Fcγ receptors on neutrophils resulting in cellular activation. Fcγ receptors and their activation have been reviewed by Ravetch, J. V. and J. P. Kinet, 1991, *Ann Rev. Immunol.* 9:457–492and Hulett, M. D. and P. M. Hogarth, 1994, *Adv. Immunol.* 57:1–127.

Agents according to the present invention that selectively inhibit alternative complement pathway activation are preferably agents that do not activate Fcγ receptors, e.g., via immune complex formation with their antigen. Such agents may be screened for their ability to activate Fcγ receptors by a variety of assays known in the art. Since superoxide generation is one of the classic responses of neutrophils and other phagocytes to activation via Fcγ receptors (RII), a specific assay for superoxide release from cells in diluted whole blood was utilized to screen and evaluate agents and the possible role of Fcγ receptors in neutrophil activation by such an agent. Monoclonal antibody agents are generally ineffective aggregating agents upon binding to their antigen and thus ineffective to activate Fcγ receptors via immune complex formation. However, Fcγ activation was detected for a blocking anti-properdin monoclonal antibody as follows.

A chemiluminescence assay for superoxide production in diluted whole blood was performed (Tose, M. F. and A. Itamedani, 1992, *Am. J. Clin. Pathol.* 97:566–573). Fresh blood was collected by a finger prick and rapidly diluted 350-fold into phenol red-free RPMI-1640 media containing Pen-Strep which was buffered with 10 mM HEPES (pH 7.4) at 37° C. The media also contains 10 μM lucigenin (Sigma Chemical Co.), a compound which becomes chemiluminescent when reduced by superoxide. Potential stimulators of oxidative burst (e.g., PMA or C5a) or buffer controls were added to duplicate 1 ml samples of the diluted blood-lucigenin-RPMI media and incubated at 37° C. for 2–3 hours. At regular intervals, chemiluminescence was monitored by transferring each sample into a liquid scintillation counter (Packard Model 1900 TR) operated in a single photon mode to determine the "cpm". Control experiments demonstrated that the specific "cpm" signal was completely inhibited by addition of 100 μg/ml superoxide dismutase (Sigma Chemical Co.) to the samples.

One important characteristic of the Fcγ receptor (RII) is that it is activated by binding of polymeric immune-complexes; monomeric IgG is ineffective. Therefore, blood cells should have to be exposed simultaneously to properdin and anti-properdin monoclonal antibody to allow immune-complex formation and consequent cellular activation via Fcγ receptors. Results from the chemiluminescence assay demonstrates that superoxide levels in diluted blood samples are not significantly elevated over control levels by addition of either 5 μg/ml properdin alone or 100 nM monoclonal antibody alone. However, simultaneous addition of both 5 μg/ml properdin and 100 nM monoclonal antibody to the diluted blood samples results in a marked increase in superoxide generation over control levels, indicating that cell activation occurs via Fcγ receptors. C5a also activates the neutrophil oxidative burst response via C5a receptors, and samples containing 10 nM C5a were positive controls in this assay. The anti-human properdin monoclonal antibody has a binding specificity for the human protein and does not bind rat properdin. Consistent with this specificity, incubation of blood samples with 5 μg/ml rat properdin and 100 nM anti-human monoclonal antibody did not elicit an increase in superoxide generation over control levels. The results of this study indicate that neutrophil activation is mediated via binding of properdin-monoclonal antibody immunecomplexes to Fcγ receptors on cells, resulting in an increased release of elastase upon addition of the monoclonal antibody to the tubing loop model.

There are several potential strategies that can be used in the design of agents according to the present invention that avoid Fcγ receptor interactions. For monoclonal antibody agents, one approach is to select the human γ4 IgG isotype during construction of a humanized antibody. The γ4 IgG isotype does not bind Fcγ receptors. Alternatively, a monoclonal antibody agent can be genetically engineered that lacks the Fc region, including for example, single chain antibodies and antigen-binding domains. Yet another approach is to chemically remove the Fc region of a monoclonal antibody using partial digestion by proteolytic enzymes, thereby generating, for example, antigen-binding antibody fragments such as Fab or F(ab)$_2$ fragments. Such antigen-binding antibody fragments and derivatives are similarly useful as potent inhibitors of alternative pathway complement activation.

In this study, proteolysis was utilized to remove the Fc region of the blocking anti-properdin monoclonal antibody described in the Examples above, which is a murine IgG1. Specifically, a procedure for generating F(ab)$_2$ from murine IgG1 using ficin digestion (Mariani, M, M. Camagna, L. Tarditi and E. Seccamani, 1991, *Mol. Immunol.* 28:69–71) was utilized. The progressive ficin-mediated cleavage of this IgG1 antibody yielded a 116 kD species corresponding to F(ab)$_2$and another species at 32 kD corresponding to the cleaved Fc region. Ficin digestion conditions were identified which resulted in the generation of F(ab)$_2$at high yield and the total absence of any detectable intact IgG band on Coomassie-stained SDS-PAGE gels.

The potency of this F(ab)$_2$ fragment as an inhibitor of complement activation was compared to that of the intact anti-properdin monoclonal antibody, using the rabbit RBC hemolysis assay as described in Example 4. The results showed that the ficin-digested monoclonal antibody preparation containing the F(ab)$_2$ fragment has essentially the identical inhibitory activity as the intact monoclonal antibody when both are tested at 3.3 nM (partial inhibition) or 6.7 nM (complete inhibition). In addition, these anti-properdin agents have essentially equivalent potency as inhibitors of C3and sMAC generation in the tubing loop model of cardiopulmonary bypass described in Example 5.

Figure 8:
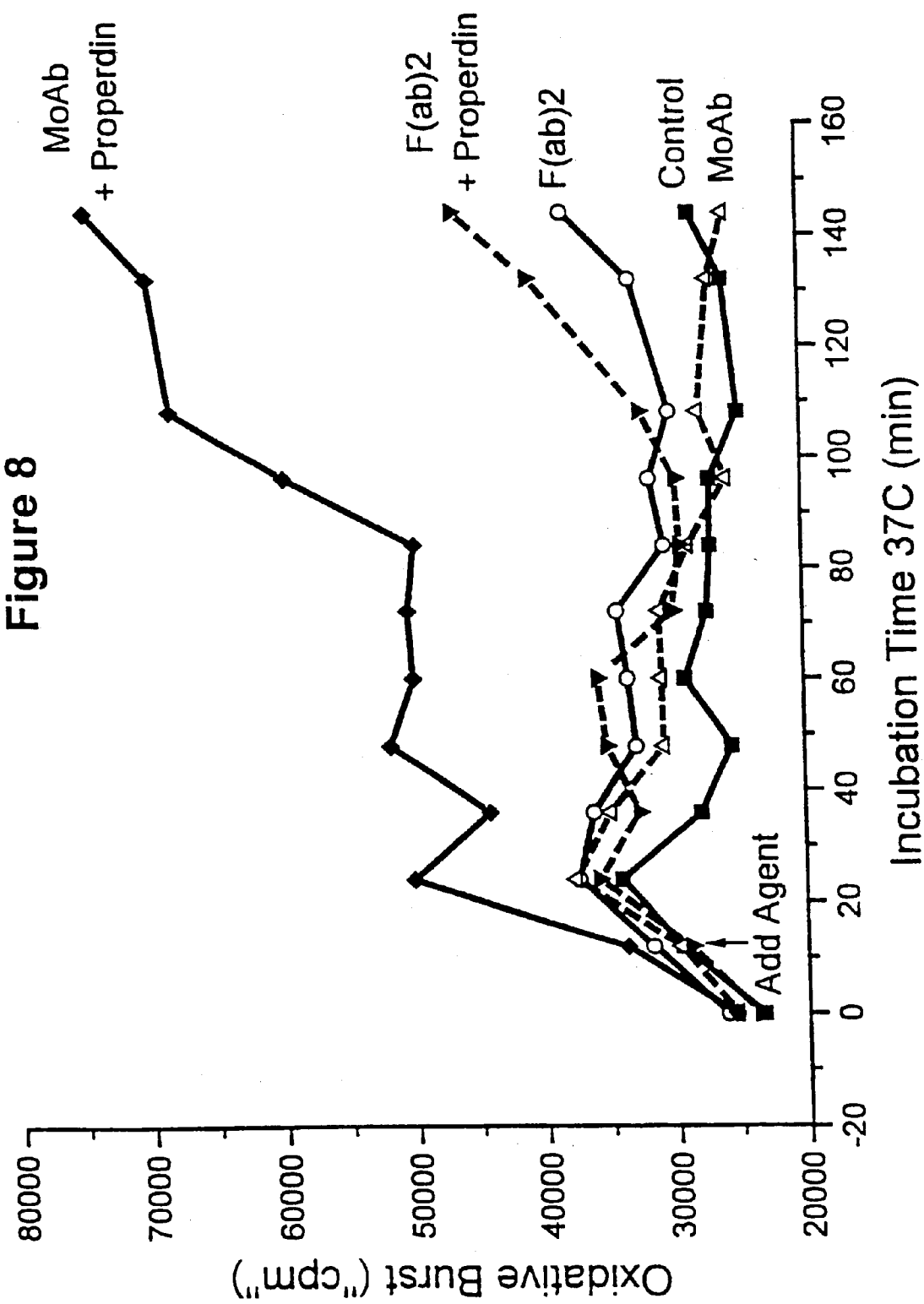
FIG. 8 shows the lack of Fcγ receptor activation as detected by lack of superoxide generation, using an $F(ab)_2$ fragment preparation of an anti-properdin monoclonal antibody with properdin.

As shown in FIG. 8, when the activity of F(ab)$_2$ and the intact antibody were compared in the superoxide generation assay using diluted blood, addition of both intact monoclonal antibody (100 nM) and properdin (5 µg/ml) to the diluted blood samples resulted in a marked increase in superoxide generation over control levels. In comparison, superoxide generation in the diluted blood samples following addition of both F(ab)$_2$ (100 nM) and properdin (5 µg/ml) was substantially reduced and was similar to superoxide generation after addition of the F(ab)$_2$ alone (FIG. 8). At later time points (>130 minutes), superoxide generation in both of the F(ab)$_2$ containing samples was slightly higher than in the control samples (FIG. 8). However, since the F(ab)$_2$ preparation was not purified to remove contaminating Fc or trace amounts of intact monoclonal antibody, small amounts of such contaminants could generate a small residual response. Fc contaminants can be removed by standard purification methods if desired. The results of this study demonstrate that generation of an antigenbinding fragment such as F(ab)$_2$ can essentially eliminate activation of blood cells via binding of Fcγ receptors.

It is of interest that this type of activation using an anti-properdin monoclonal antibody has not been noted with other anti-complement monoclonal antibodies. For example, a monoclonal antibody to C5 has been shown to block the classical and alternative complement pathways where they converge at C5 (the terminal complement pathway) by blocking the cleavage of C5, thus preventing production of MAC and C5a (WO95/25540 [PCT/US95/03614]; Rinder, et al., supra (1995)).

According to the present invention, preferred therapeutic agents may be screened and prepared that lack such Fcγ receptor activation and are particularly effective in processes for selective inhibition of the formation of alternative complement pathway activation products. In addition, agents according to the present invention are preferably agents that are selective for their inhibition of formation of alternative pathway activation products (i.e., do not inhibit classical pathway components) and that do not activate the classical complement pathway. Immune complexes, in addition to activating cells via binding to Fcγ receptors, can trigger the classical pathway of complement activation by binding to complement component C1. To show that the classical pathway of complement activation was not activated by the blocking anti-properdin monoclonal antibody described above, duplicate samples of normal human serum (NHS) were incubated at 37° C. for 120 minutes with or without 200 nM anti-properdin monoclonal antibody (30 µg/ml). At 0, 30, 60, and 120 minutes, 50 µl aliquots were removed from the mixture and chelated by the addition of EDTA to a final concentration of 13 mM in order to stop all magnesium- and calcium-dependent complement activation. The concentration of the complement activation product C3a was determined in all samples using an ELISA kit following the manufacturer's instructions (Quidel, Catalog No. A015). None of the samples containing the anti-properdin monoclonal antibody had elevated C3a levels compared to corresponding control samples. These results demonstrate that blocking anti-properdin monoclonal antibody does not trigger activation of the classical pathway. Furthermore, these results suggest that the structural determinants on immune complexes recognized by C1 are different than those recognized by Fcγ receptors. Preferred agents according to the invention are therefore agents that do not substantially activate Fcγ receptors or the classical complement pathway as shown herein.

EXAMPLE 7

Classical Pathway Activation: Heparin—Protamine Complexes

Protamine addition to heparinized blood has been shown to activate the classical complement pathway (Cavarocchi, N. C., H. V. Schaff, T. A. Orszulak, H. A. Homburger, W. A. Schnell, and J. R. Pluth, 1985, *Surgery* 98:525–531. Thus, complement activation occurs not only during blood circulation through tubing for a bypass circuit like that utilized in Example 5above, but also after the addition of protamine (to neutralize anticoagulant heparin) at the end of the CPB procedure. To evaluate the effect of protamine on generation of soluble MAC, heparinized blood was incubated in tubes at 37° C. for 60 minutes with 100 µg/ml protamine either in the absence or presence of a blocking anti-properdin monoclonal antibody as described in Examples 1–5above. Samples were processed and analyzed for sMAC generation using an ELISA kit following the manufacturer's instructions (Quidel, Catalog No. A009).

Figure 9:
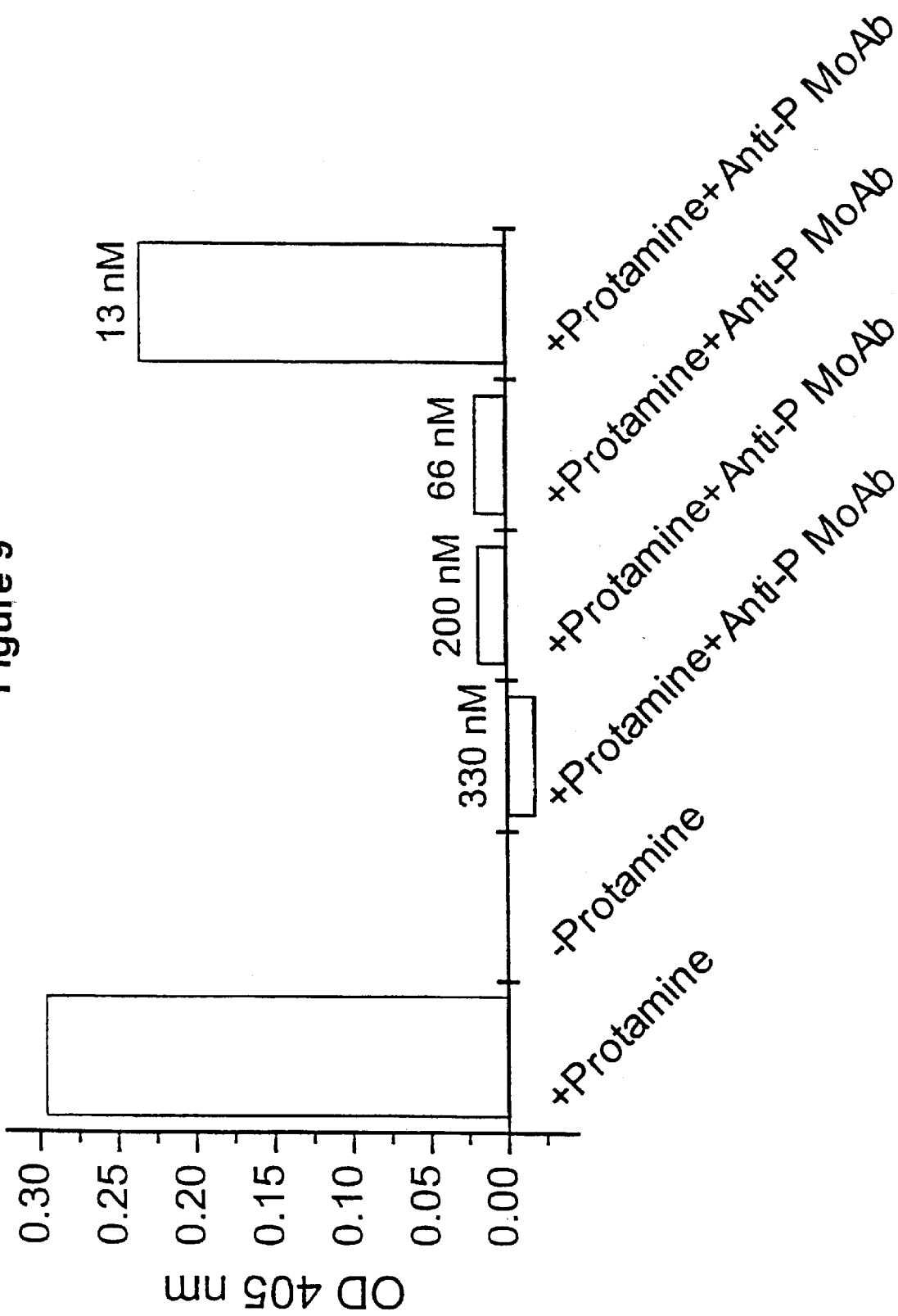
FIG. 9 shows the inhibition of the formation of alternative complement pathway activation products, including MAC, initiated by heparin-protamine complexes using an anti-properdin monoclonal antibody.

As shown in FIG. 9, the anti-properdin monoclonal antibody inhibits complement activation initiated by heparin-protamine complexes, under conditions where fresh heparinized blood was incubated as described above in tubes at 37° C. for 60 minutes with 100 µg/ml protamine either in the absence of presence of 13, 66, 200 or 330 nM anti-properdin monoclonal antibody and as detected by sMAC generation.

Because complement activation occurs not only during the movement of blood through a bypass circuit, but also after the addition of protamine upon completion of CPB, and because this latter activation involves the classical complement pathway (Cavarocchi, N. C., H-V. Schaff, T. A. Orszulak, H. A. Homburger, W. A. Schnell, and J. R. Pluth, 1985, *Surgery* 98:525–531), it was unexpected that an alternative pathway-specific anti-properdin agent would attenuate or substantially inhibit the production of complement activation products triggered by heparin-protamine complexes as shown in FIG. 9.

Although it has been suggested that the alternative pathway might contribute somewhat to the classical pathway-initiated production of terminal activation products because the alternative pathway C3 convertase could, in theory, be assembled from C3b generated in the classical cascade, there has been a general paucity of experimental data addressing this hypothesis. A relatively recent study has more definitively addressed the question of alternative pathway contribution to the classical pathway, particularly as it pertains to the role of properdin. Specifically, Fredrikson et al. (1993) examined the effect of properdin deficiency on the amount of MAC generated after activation of the classical pathway. Their results reveal that the absence of properdin in serum had no effect on classical pathway production of MAC. In contrast, depletion of classical pathway components (i.e., C1q, C2, C4) completely abolished MAC generation in their assay system. These results indicate that inhibiting properdin action with an anti-properdin agent should have no effect on the production of activated complement species after initiation of the classical pathway by protamine-heparin complexes. Further support for this interpretation is supplied by the work of Soderstrom, C., J. H. Braconier, D. Danielsson, and A. G. Sjoholm, 1987, *J. Infect. Dis.* 156:107–112, who showed that serum bactericidal reactions mediated via the classical complement pathway were not impaired in properdin-deficient serum. These results specifically teach that inhibiting properdin action should have little, if any, effect on the production of complement activation proteins after initiation of the classical complement pathway. More generally, these data imply that the alternative pathway contributes negligibly to the classical pathway-induced production of complement activation products. This more general interpretation is supported by the work of Clardy, C. W., 1994, *Infect. Immun.* 62:4549–4555, who reported that an antibody to the alternative pathway-specific component, factor B, had no effect on classical pathway complement activation.

In agreement with what is seen during clinical CPB and as shown above, protamine addition to heparinized human blood causes significant complement activation, as measured by the production of sMAC (FIG. 9). Remarkably, addition of the anti-properdin antibody to the heparinized blood prior to the addition of protamine results in nearly complete inhibition of sMAC formation (FIG. 9) and demonstrates that an anti-properdin agent is effective in reducing the post-perfusion complications associated with CPB since it is capable of inhibiting both classical and alternative complement pathways.

EXAMPLE 8

Classical Pathway Activation: Immune Complexes

The classical complement pathway is typically triggered by immune complexes, for example, an antibody bound to a foreign particle, and thus requires prior exposure to that particle for the generation of specific antibody. There are four plasma proteins involved in the initial steps of the classical pathway: C1, C2, C4 and C3. The interaction of C1 with the Fc regions of IgG or IgM in immune complexes activates a C1 protease that can cleave plasma protein C4, resulting in the C4a and C4b fragments. C4b can bind another plasma protein, C2. The resulting species, C4b2, is cleaved by the C1 protease to form the classical pathway C3 convertase, C4b2a. Addition of the C3 cleavage product, C3b, to the C3 convertase leads to the formation of the classical pathway C5 convertase, C4b2a3b. To evaluate the effect of immune complexes on the generation of C3a and soluble MAC, immune complexes were prepared by incubating rabbit anti-ovalbumin IgG (28 mg) (Biodesign, Kennebunk, ME) and ovalbumin (0.67 mg) (Sigma Chemical Company) in 3 ml PBS for 3 day at 4° C. to allow maximum precipitation. Preliminary experiments demonstrated that this ratio of reagents corresponds to the equivalence point for the antigen-antibody reaction. The precipitate was collected by centrifugation at 15,000 rpm for 5 min at 4° C. and washed 3 times by resuspension in 5 ml of PBS and recentrifugation. The final precipitate was resuspended in PBS at 1 mg/mil and frozen in aliquots at −70° C. SDS-PAGE analysis confirmed that the precipitate contains essentially only antibody and antigen.

To test the effect of an anti-properdin monoclonal antibody on conditions of complement activation where the classical pathway is initiated by immune complexes, triplicate 50 µl samples containing 90% NHS were incubated at 37° C. in the presence of 10 µg/ml immune complex (IC) or PBS, and parallel triplicate samples (+/−IC) also contained 200 nM anti-properdin monoclonal antibody during the 37° C. incubation. After two hour incubation at 37° C., 13 mM EDTA was added to all samples to stop further complement activation and the samples were immediately cooled to 5° C. The samples were stored at −70° C. prior to being assayed for complement activation products (C3a and sC5b-9) using ELISA kits (Quidel, Catalog Nos. A015 and A009) following the manufacturer's instructions. The results of a sMAC assay are shown in FIG. 10.

Figure 10:
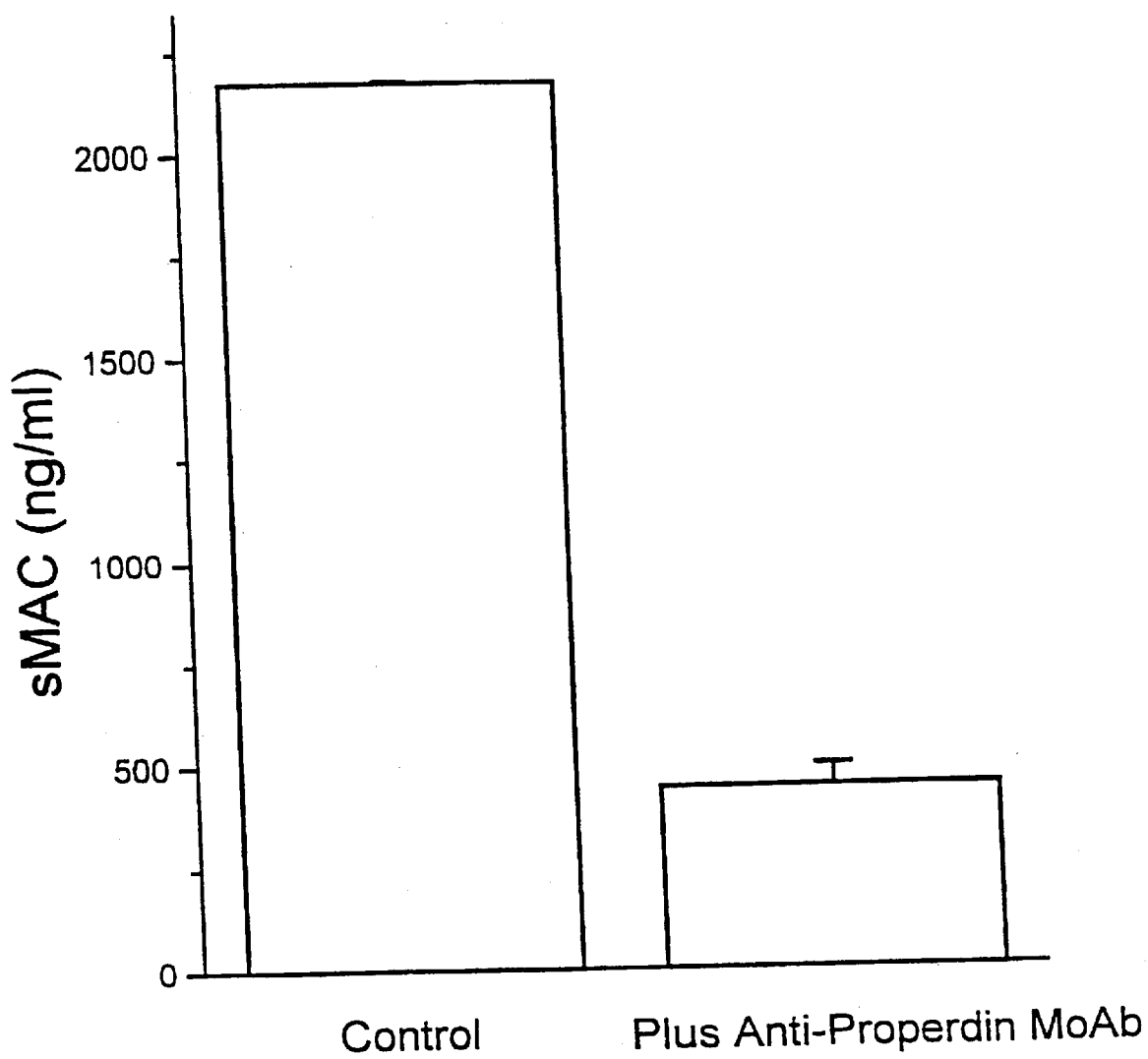
FIG. 10 shows the inhibition of the formation of alternative complement pathway activation products, including MAC, initiated by ovalbumin/anti-ovalbumin immune complexes using an anti-properdin monoclonal antibody.

Surprisingly, the addition of an anti-properdin monoclonal antibody to the serum prior to the addition of immune complexes substantially inhibited (e.g., ≧50%) both C3a and sMAC formation (approximately 80% for sMAC as shown in FIG. 10). Similar to the results described in Example 7 above with heparin-protamine complexes, it was likewise unexpected that an alternative pathway-specific anti-properdin agent would attenuate or substantially inhibit the production of activated complement species after initiation of the classical pathway by immune complexes as shown in FIG. 10.

EXAMPLE 9

Cardiopulmonary Bypass: Ex Vivo Extracorporeal Circulation

To further confirm the usefulness of anti-properdin agents, including anti-properdin antibody agents, in reducing complement activation during CPB and other extracorporeal procedures, which involve passing circulating blood from a blood vessel of a subject, through a conduit and back to a blood vessel of the subject, studies were performed in which freshly-collected human blood was passed through a circuit that is identical to that which is typically used during surgical procedures requiring pediatric extracorporeal circulation. An $F(ab)_2$ anti-properdin agent prepared as described in Example 6 was used in these studies.

Pediatric extracorporeal circuits were assembled using a hollow-fiber pediatric membrane oxygenator (Lilliput oxygenator), polyvinyl chloride tubing, polycarbonate connectors, and a minimally occlusive roller pump. Oxygenator and circuitry were primed with 400 mnl of Plasmalyte. Blood (225 ml) was drawn from a healthy volunteer into a transfer pack containing 1000 U heparin which was then added to the extracorporeal circuit. For studies of complement inhibition during extracorporeal circulation, a $F(ab)_2$ preparation of an anti-properdin monoclonal antibody in PBS (~25 µg/ml of blood) was added to the transfer pack immediately before addition of blood to the extracorporeal circuit. As blood was introduced to the reservoir via the prime port, 225 ml of prime fluid was simultaneously withdrawn distal to the oxygenator outlet to yield a final circuit volume of 400 ml and a final hematocrit of 20%. Blood was circulated with prime, and complete mixing was accomplished within 2 minutes. A baseline sample was drawn and designated as time 0. The circuit was maintained at 37° C. for 30 minutes, then cooled to 28° C. over five minutes and maintained at that temperature for 60 minutes, after which it was rewarmed to 37° C. for an additional 60 minutes. Blood samples were drawn at multiple times during recirculation. Serum samples were prepared by immediate centrifugation, and stored at −70° C. in aliquots until assayed for C3a or sMAC via ELISA kits following the manufacturer's instructions (Quidel: C3a kit, Catalog No. A015; sMAC kit, Catalog No. A009) or neutrophil elastase using an ELISA as described by Brower, M. S. and P. C. Harpel, 1983, Blood 61:842–849.

As shown in FIG. 11, an F(ab)$_2$ preparation of a blocking anti-properdin monoclonal antibody inhibits complement activation in an ex vivo model of CPB where fresh human blood was pumped through a pediatric bypass circuit either in the absence (closed circles) or presence (open circles) of an F(ab)$_2$ preparation of an anti-properdin monoclonal antibody. As described above, blood samples were collected at various times during the bypass procedure and analyzed for sMAC, C3a or elastase-antitrypsin complexes.

For this study, the two bypass circuits that were utilized were connected to a common non-pulsatory pump such that blood flow was identical in the two systems. Whereas one circuit contained untreated blood, the other contained blood to which the anti-properdin agent was added prior to the onset of circulation. In addition in this study, a F(ab)$_2$ preparation of the anti-properdin monoclonal antibody was utilized to ensure that properdin-anti-properdin complexes did not trigger cellular signal transduction events by binding to Fcγ receptors. This F(ab)$_2$ antibody fragment was prepared by proteolytic cleavage with ficin as described in Example 6. Standard proteolytic methodologies as well as standard recombinant methodologies may be used to prepare antibody-based proteins, including fragments, derivatives, single chain antibodies (SCA) and antigen-binding domains that lack the Fc portion of the immunoglobulin that allows binding to Fcγ receptors (Janeway, C. and P. Travers, Jr., 1994, *Immunobiology: the Immune System in Health and Disease*. pp 3:28–3:30. Garland Publishing, Inc., New York). Alternatively, the potential binding of therapeutic antibodies Fcγ receptors can be eliminated, if desirable or necessary, by utilizing antibodies of the γ4 sub-class of IgG, which do not interact with these receptors (Janeway, C. and P. Travers, Jr., supra (1994)).

As demonstrated in FIG. 11, the onset of blood flow in this ex vivo model of CPB resulted in the rapid production of sMAC and C3a, with the levels of these activated complement components increasing as a function of bypass time. Likewise, blood levels of elastase-antitrypsin complexes, a marker of neutrophil activation (Finn, A., S. Naik, N. Klein, R. J. Levinsky, S. Strobel, and M. Elliott, 1993, *J. Thorac. Cardiovasc. Surg.* 105:234–241), increased with circulation time in the CPB circuit (FIG. 9). It has been postulated that neutrophil activation during CPB results from the binding of complement activation species to these cells (Rinder, C. S., H. M. Rinder, B. R. Smith, J. C. K. Fitch, M. J. Smith, J. B. Tracey, L. A. Matis, S. P. Squinto, and S. A. Rollins, S. A., 1995, *J. Clin. Invest.* 96:1564–1572; Wan, S., J-L. LeClerc, and J-L. Vincent, 1997, *Chest* 112:676–692). The parallel circuit containing blood treated with the F(ab)$_2$ anti-properdin monoclonal antibody preparation showed essentially no complement activation, as revealed by the virtual absence of sMAC and C3a at all bypass times. Importantly F(ab)$_2$ anti-properdin also caused a reduction in neutrophil activation, as demonstrated by the reduction in blood elastase-antitrypsin complex levels (FIG. 11). These results confirm the results obtained with the tubing loop model described in Example 5 above. These results further demonstrate that an anti-properdin agents that lacks Fcγ receptor activation ability effectively reduces the complement activation and related cellular inflammatory events that result from extracorporeal circulation and subsequent protamine complexation of heparin.

EXAMPLE 10

Blocking Agents: Screening of Properdin-Derived Peptides

Several decapeptides of human properdin as described by Fredrikson, et al., supra (1996) were prepared and tested for their ability to block the effects of alternative complement pathway activation as described for anti-properdin antibodies in the Examples above. Specifically, these properdin-derived peptides were assayed for their ability to inhibit MAC formation in an ELISA as described in Example 3. Peptide 1 consisting of amino acids 43–52 of properdin (1158 M.W.), peptide 2 consisting of amino acids 48–57 of properdin (1320 M.W.) and peptide 3 consisting of amino acids 73–82 of properdin (1309 M.W.) each reduced MAC formation in this assay, with IC$_{50}$ values of 268 μM, 335 μM and 242 μM, respectively. In contrast, peptide 4 consisting of amino acids 218–227 of properdin (1173 M.W.) did not similarly inhibit MAC formation in this assay (IC$_{50}$>600 μM). When these four peptides were tested as described in Example 2above, peptides 1, 2 and 3, but not peptide 4, blocked C3bBb binding, with the IC$_{50}$ for the 3 blocking peptides in the range of about 400–600 μM.

In a previous study by Fredrikson, et al., supra (1996) to characterize a dysfunctional properdin protein from a patient with Type III properdin deficiency, 87 overlapping decapeptides of human properdin, including the four peptides described above, were synthesized. When these peptides assayed at concentrations of 0–200 μg/ml for their ability to compete with the binding of properdin to C3b coated plates, five peptides designated as 9, 10, 15, 44 (corresponding to peptides 1, 2, 3 and 4 herein) and 81 were determined by Fredrikson, et al., supra (1996) to compete with properdin for C3 binding. These peptides were not tested in assays of complement activation, such as the MAC formation assay described above.

Since properdin has now been demonstrated according to the present invention to be a critical component for activation of the alternative pathway, anti-properdin agents, including properdin-derived peptides, may be screened, identified and selected for their ability to block alternative pathway activation, as demonstrated herein, for example, by blocking MAC formation. Since the screening assay showed that inhibition of MAC formation was essentially complete at the higher peptide concentrations, properdin was again demonstrated to be required for activation of the alternative pathway. Anti-properdin agents, including properdin-derived peptides, may be identified according to the present invention as effective agents in a process for selectively inhibiting the generation (i.e., formation or production) of an alternate complement pathway activation product in a subject in which either the alternative pathway or the classical pathway has been initiated, including in subjects with a variety of disease states and conditions, as well as complications from a variety of medical procedures, and including subjects with acute and/or chronic pathological injuries as described and referenced herein.

EXAMPLE 11

Blocking Agents: Screening and Identification

Agents, which selectively block the formation of complement activation products via the alternative complement pathway, including preferred anti-human properdin antibodies, may be obtained and then screened, identified and selected as taught herein, for their ability to substantially or completely block the formation or production of alternative complement pathway-dependent activation products, including in conditions involving initiation of the classical complement pathway.

Seven commercially available anti-human properdin monoclonal antibodies were screened for blocking activity:

(1) Quidel anti-human Factor P#1 (A233); (2) Quidel anti-human Factor P#2 (A235); (3) Dako (Santa Barbara, Calif.) anti human Factor P (MO837); (4) Serum Institute (Copenhagen, Denmark) anti-human Factor P (HYB039 Clone 06); (5) Serum Institute anti-human Factor P (HYB039 Clone 04); (6) Biogenesis (Poole, UK) anti-human Factor P (Clone 10–18) [same as Quidel #1]; and Biogenesis anti-human Factor P (Clone 10–24) [same as Quidel #2]. Each of these seven antibodies were able to bind to properdin with high affinity ($K_D \approx 0.1-1$ nM). However, only the Quidel P#1 monoclonal antibody (and the identical monoclonal antibody (Clone 10–18) from Biogenesis) completely blocked alternative pathway complement activation, as detected by complete inhibition of MAC formation. The Serum Institute HYB039 clone 04 was found to only partially block and increasing the concentration of this monoclonal antibody did not achieve complete blocking. This partially blocking monoclonal antibody and the completely blocking Quidel #1 monoclonal antibody have comparable binding affinities for properdin ($K_D \approx 0.1-0.2$ nM). According to the present invention, agents are therefore effectively screened for essentially complete, partial or no blocking activity in one or more assays as described herein, including blocking of C3b binding (Example 1), blocking of C3bBb binding (Example 2), blocking of alternative pathway-dependent MAC formation (Examples 3 and 5–7), blocking of alternative pathway-dependent hemolysis (Example 4), blocking of alternative pathway-dependent C3a formation (Examples 5–7), or blocking of one or more markers of alternative pathway-dependent cell activation (Example 7), including markers of leukocyte activation (e.g., elastase-antitrypsin, CD11b/CD18), platelet activation (e.g., P-selection, GPIIIa, GPIb (CD45b), GPIIb) and platelet-leukocyte adhesion. Agents may be further screened for lack of activation of Fcγ receptors and/or classical pathway activation (Example 6).

What is claimed is:

1. A process of inhibiting the adverse effects of alternative complement pathway activation products in a subject comprising administering to the subject an amount of anti-properdin agent effective to selectively inhibit formation of an alternative complement pathway activation product.

2. The process of claim 1 wherein the amount of the anti-properdin agent is effective to selectively inhibit formation of MAC.

3. The process of claim 1 wherein the amount of the anti-properdin agent is effective to selectively inhibit formation of C3a or C5a.

4. The process of claim 1 wherein the anti-properdin agent is an anti-properdin antibody.

5. The process of claim 1 wherein the anti-properdin agent is an antigen-binding fragment of an anti-properdin antibody.

6. The process of claim 1 wherein the anti-properdin agent is an properdin-derived peptide.

7. The process of claim 1 wherein the anti-properdin agent lacks the ability to activate Fcγ receptors.

8. A process for inhibiting the adverse effects of classical complement pathway activation in a subject in which the classical complement pathway is initiated comprising administering to the subject an amount of an anti-properdin agent effective to selectively inhibit formation of an alternative complement pathway activation product.

9. The process of claim 8 wherein the amount of the anti-properdin agent is effective to selectively inhibit formation of MAC.

10. The process of claim 8 wherein the amount of the anti-properdin agent is effective to selectively inhibit formation of C3a or C5a.

11. The process of claim 8 wherein the anti-properdin agent is an anti-properdin antibody.

12. The process of claim 8 wherein the anti-properdin agent is an antigen-binding fragment of an anti-properdin antibody.

13. The process of claim 8 wherein the anti-properdin agent is a properdin-derived peptide.

14. The process of claim 8 wherein the anti-properdin agent lacks the ability to activate Fcγ receptors.

* * * * *